United States Patent
Cheon et al.

(10) Patent No.: US 7,745,439 B2
(45) Date of Patent: Jun. 29, 2010

(54) INDENE DERIVATIVES AND PROCESS FOR THE PREPARATION THEREOF

(75) Inventors: Hyae Gyeong Cheon, Daejeon (KR); Sung-Eun Yoo, Kongju-si (KR); Sung Soo Kim, Daejeon (KR); Sung-Don Yang, Daejeon (KR); Kwang-Rok Kim, Daejeon (KR); Sang Dal Rhee, Daejeon (KR); Jin Hee Ahn, Daejeon (KR); Seung Kyu Kang, Daejeon (KR); Won Hoon Jung, Daejeon (KR); Sung Dae Park, Seoul (KR); Nam Gee Kim, Seoul (KR); Sun Mee Kim, Suwon-si (KR); Kil Woong Mo, Seoul (KR); Jae Mok Lee, Seoul (KR); Hye Jung Kang, Suwon-si (KR); Koun Ho Lee, Seoul (KR); Jong Hoon Kim, Anyang-si (KR); Jeong-Hyung Lee, Daejeon (KR); Seung Jun Kim, Daejeon (KR)

(73) Assignees: Korea Research Institute of Chemical Technology, Daejeon (KR); Jeil Pharm. Co., Ltd., Seoul (KR); Korea Research Institute of Bioscience and Biotechnology, Daejeon (KR); CJ Corp., Seoul (KR)

( * ) Notice: Subject to any disclaimer, the term of this patent is extended or adjusted under 35 U.S.C. 154(b) by 28 days.

(21) Appl. No.: 10/599,913

(22) PCT Filed: Apr. 12, 2005

(86) PCT No.: PCT/KR2005/001051
§ 371 (c)(1), (2), (4) Date: Oct. 23, 2006

(87) PCT Pub. No.: WO2005/100297
PCT Pub. Date: Oct. 27, 2005

(65) Prior Publication Data
US 2007/0225288 A1    Sep. 27, 2007

(30) Foreign Application Priority Data
Apr. 13, 2004  (KR) ............... 10-2004-0025218

(51) Int. Cl.
- A61K 31/216 (2006.01)
- A61K 31/4402 (2006.01)
- A61K 31/5375 (2006.01)
- C07C 69/753 (2006.01)
- C07D 211/70 (2006.01)
- C07D 265/32 (2006.01)

(52) U.S. Cl. ............... 514/239.2; 514/277; 514/510; 544/174; 546/339; 560/56

(58) Field of Classification Search ............... None
See application file for complete search history.

(56) References Cited

U.S. PATENT DOCUMENTS 3,642,785 A * 2/1972 Shen et al. ............ 548/473
6,448,260 B2 * 9/2002 Cousins et al. ............ 514/299

FOREIGN PATENT DOCUMENTS

WO    WO 93/08799    *  5/1993

OTHER PUBLICATIONS

Barvian et al.: 1-Oxo-3-aryl-1H-indene-2-carboxylic acid derivatives as selective inhibitors of fibroblast growth factor receptor-1 tyrosine kinase. Bioorganic & Medicinal Chemistry Letters, vol. 7, No. 22, p. 2903-2908, 1997.*
Rayabarapu et al.: Regioselective Synthesis of Indenols via Nickel-Catalyzed Carbocyclization Reaction. J Org Chem, vol. 68, p. 6726-6731, 2003.*
Berger et al.: The Mechanisms of Action of PPARs. Annu Rev Med, vol. 53, p. 409-435, 2002.*
C.F. Koelsch, Electrophilic Properties of Ethyl 3-Phenylindone-2-carboxylate, XP-002470836, pp. 2088-2091, (1960).
Andrea Cappelli, et al., Synthesis and Characterization of a New Benzofulvene Polymer . . . , JOC Notes, XP-002462155, pp. 9473-9476, (2003).
Kuo-Jui Chang, et al., Cobalt-catalyzed regioselective carbocyclization reaction of o-iodophenyl ketones . . . , XP-002470837, p. 1, (2004).
Dinesh Kumar Rayabarapu et al., Nickel-catalyzed regioselective carbo- cyclization of ortho-halophenyl ketones . . . , XP-002470838, p. 1, (2002).
M.R. Barvian et al., 1-oxo-3-aryl-1H-indene-2-carboxylic acid derivatives as selective inhibitors of fibroblast . . . , XP-002470839, p. 1, (1997).
Jose Vicente et al., Palladium-assisted formation of carbon-carbon bonds, XP-002470840, p. 1, (1996).

\* cited by examiner

Primary Examiner—Brian-Yong S Kwon
Assistant Examiner—Bong-Sook Baek
(74) Attorney, Agent, or Firm—Sughrue Mion, PLLC

(57) ABSTRACT

The inventive indene derivatives of formula (I) are capable of selectively modulating the activities of peroxisome proliferator activated receptors (PPARs), causing no adverse side effects, and thus, they are useful for the treatment and prevention of disorders modulated by PPARs, i.e., metabolic syndromes such as diabetes, obesity, arteriosclerosis, hyperlipidemia, hyperinsulinism and hypertension, inflammatory diseases such as osteoporosis, liver cirrhosis and asthma, and cancer.

3 Claims, No Drawings

INDENE DERIVATIVES AND PROCESS FOR THE PREPARATION THEREOF

FIELD OF THE INVENTION

The present invention relates to a novel indene derivative, which is useful as a modulator of a peroxisome proliferator activated receptor (PPAR), a process for the preparation thereof and a pharmaceutical composition containing same as an active ingredient.

BACKGROUND OF THE INVENTION

Peroxisome proliferator activated receptors (PPARs) are members of the nuclear hormone receptor superfamily and function as transcription factors regulating gene expression in a form of heterodimers with retinoid X receptors (RXRs). The PPARs are divided into three subtypes, "PPARα", "PPARγ" and "PPARδ", and are generally involved in maintaining energy homeostasis in vertebrates through the control of fat and glucose metabolisms.

Accordingly, many attempts have been made to develop PPARα and PPARγ full agonists which are useful for the treatment and prevention of disorders modulated by PPARs, e.g., metabolic syndromes such as diabetes, obesity, arteriosclerosis, hyperlipidemia, hyperinsulinism and hypertension; inflammatory diseases such as osteoporosis, liver cirrhosis and asthma; and cancer.

For example, it has been reported that thiazolidine-2,4-dione (TZD) and non-TZD-based full agonists on PPARγ exhibit excellent blood glucose level-lowering effect in non-insulin dependent diabetes mellitus (NIDDM) mammal models (*J. Med. Chem.*, 1999, 42, 3785; *Bioorg. Med. Chem. Lett.*, 2000, 2453; *Chem. Pharm. Bull.*, 2002, 50, 1349; *Bio. Med. Chem. Lett.*, 2002, 77; *J. Med. Chem.*, 2003, 46, 3581).

However, such a PPARγ full agonist is also known to cause adverse side effects including weight gain due to facilitation of fat cell differentiation, cardiac hypertrophy, edema and liver damage.

Therefore, there exists a need to develop selective PPAR modulators (SPPARMs) which are capable of selectively controlling activities of the PPARs without causing side effects (*Molecular Cell*, 2001, 8, 737; *Molecular Endocrinology*, 2003, 17, 662; *Molecular Endocrinology*, 2002, 16, 2628).

SUMMARY OF THE INVENTION

Accordingly, it is a primary object of the present invention to provide a novel compound, which is capable of selectively modulating the activities of peroxisome proliferator activated receptors (PPARs), causing no adverse side effects.

It is another object of the present invention to provide a process for the preparation of said compound.

It is a further object of the present invention to provide a pharmaceutical composition containing said compound as an active ingredient.

In accordance with one aspect of the present invention, there is provided a novel indene derivative of formula (I) or a pharmaceutically acceptable salt thereof:

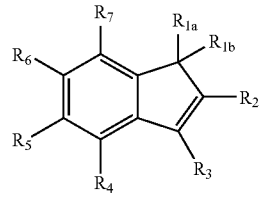

wherein, $R_{1a}$ is OH or H;

$R_{1b}$ is $C_{1-6}$ alkyl, $C_{3-6}$ cycloalkyl, benzyl or phenyl, the phenyl being optionally substituted with one or more substituents selected from the group consisting of halogen, CN, $NH_2$, $NO_2$ and $OR^a$, when $R_{1a}$ is OH; when $R_{1a}$ is H, $R_{1b}$ is $OR^a$, $NR^bR^c$, $NHCOR^a$ or

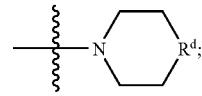

$R_2$ is CN, $CO_2R^a$ or $CONR^eR^f$;

$R_3$ is phenyl optionally substituted with one or more substituents selected from the group consisting of halogen, CN, $NH_2$, $NO_2$, $OR^a$ and $C_{1-6}$ alkyl; and $R_4$, $R_5$, $R_6$ and $R_7$ are each independently H, $O(CH_2)_mR^g$ or $CH_2R^h$;

in which $R^a$ is H, $C_{1-6}$ alkyl or $C_{3-6}$ cycloalkyl, the $C_{1-6}$ alkyl and $C_{3-6}$ cycloalkyl being optionally substituted with one or more halogens;

$R^b$, $R^c$, $R^e$ and $R^f$ are each independently H, $C_{1-6}$ alkyl, $C_{3-6}$ cycloalkyl or benzyl;

$R^d$ is O, S or $NR^a$;

$R^g$ is H,

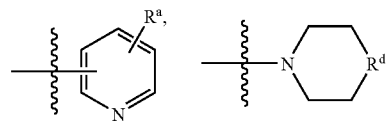

or phenyl, the phenyl being optionally substituted with one or more substituents selected from the group consisting of halogen, CN, $NH_2$ and $NO_2$;

$R_h$ is

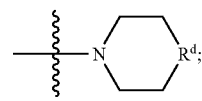

and m is an integer in the range of 1 to 3.

DETAILED DESCRIPTION OF THE INVENTION

The indene derivatives of the present invention may include optical isomers of the compound of formula (I).

Also, the pharmaceutically acceptable salt of the inventive indene derivative is a non-toxic addition salt generated from an inorganic acid such as hydrochloric acid, an organic acid such as trifluoroacetic acid, citric acid, lactic acid, maleic acid and fumaric acid, an inorganic base such as an alkali or alkaline earth metal (e.g., sodium, potassium, magnesium and calcium) hydroxides, bicarbonates and carbonates, or an organic base such as amines.

Among the compounds of formula (I) of the present invention, preferred are those wherein $R_{1b}$ is $C_{1-6}$ alkyl, $C_{3-6}$ cycloalkyl, benzyl or phenyl, the phenyl being optionally substituted with one or more methoxy groups, when $R_{1a}$ is OH; when $R_{1a}$ is H, $R_{1b}$ is $OR^a$, $NR^bR^c$, $NHCOR^a$ or

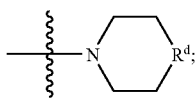

$R_3$ is phenyl being optionally substituted with one or more halogens or $C_{1-4}$ alkyls; and $R_4$ and $R_7$ is H, in which $R^a$ is H or $C_{1-6}$ alkyl; $R^d$ is O or S; $R^g$ is H, phenyl,

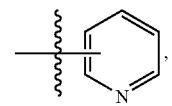

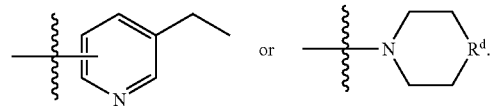

More preferred are those wherein $R_3$ is phenyl; $R_5$ is H; and $R_6$ is $O(CH_2)_mR^g$ or $CH_2R^h$.

The present invention also provides processes for preparing indene derivatives of formula (I).

The inventive compound of formula (I) may be prepared, for example, as shown in Reaction Schemes 1 or 2 as described below:

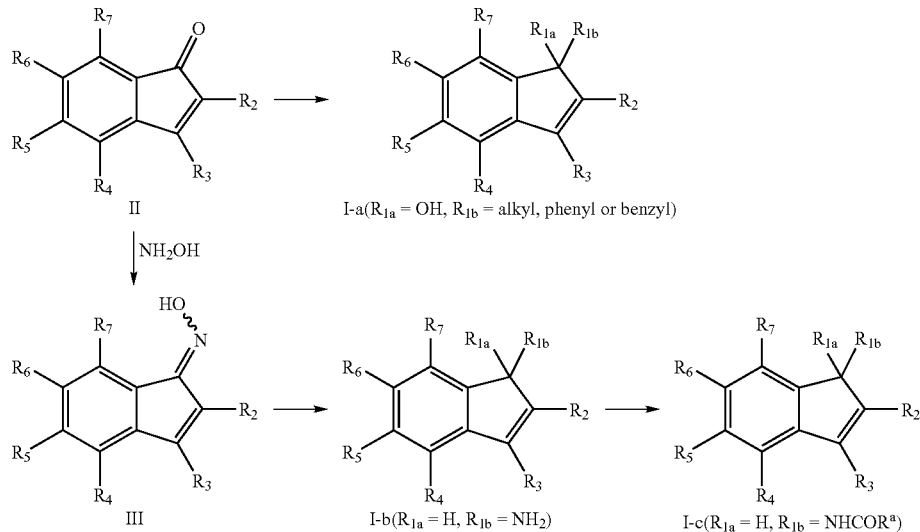

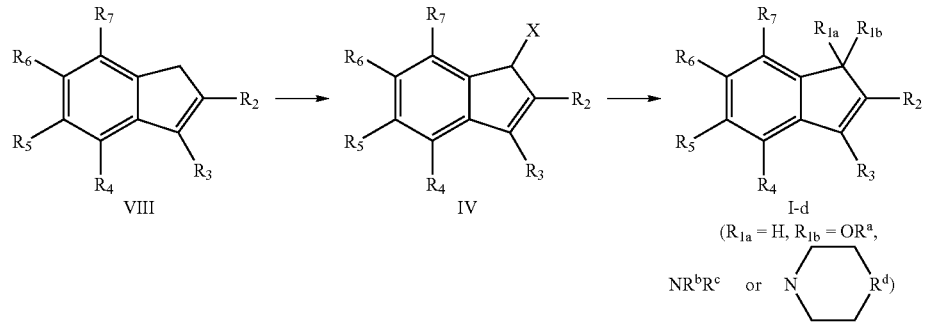

wherein, $R_{1a}$, $R_{1b}$, $R_2$, $R_3$, $R_4$, $R_5$, $R_6$ and $R_7$ have the same meanings as defined in formula (I), and X is halogen.

In Reaction Scheme 1, the compound of formula (I-a), i.e., a compound formula (I) wherein $R_{1a}$ is OH and $R_{1b}$ is alkyl, phenyl or benzyl, may be prepared by reacting the compound of formula (II) with RMgX or RLi (R=alkyl or aryl, and X=halogen), preferably with a Grignard reagent (RMgX) in a solvent.

The solvent that can be used in this reaction is tetrahydrofuran (THF) or diethyl ether, and the reaction may be carried out at a temperature in the range of 0° C. to room temperature for 1 hour or less.

Further, in Reaction Scheme 1, the compound of formula (I-b), i.e., a compound formula (I) wherein $R_{1a}$ is H and $R_{1b}$ is $NH_2$, may be prepared by (1a) reacting the compound of formula (II) with hydroxyl amine to obtain the corresponding compound of formula (III), and (1b) reacting the compound of formula (III) with hydrogen in the presence of catalyst, e.g., Pt/C, Pd or Raney nickel.

Reaction (1a) may be conducted in a solvent, e.g., methanol or ethanol at a temperature in the range of room temperature to the boiling point of the solvent until the compound of formula (II) is entirely consumed. In reaction (1b), hydrogen may be provided using a balloon and the reaction may be carried out using a solvent, e.g., methanol or ethanol at a temperature in the range of 10 to 30° C. for 1 to 24 hours.

Also, as shown in Reaction Scheme 1, the compound of formula (I-c), i.e., a compound formula (I) wherein $R_{1a}$ is H and $R_{1b}$ is $NHCOR^a$, may be prepared by reacting the compound of formula (I-b) with acetyl chloride or anhydrous acetic acid in a solvent in the presence of a base.

The solvent that can be used in the reaction is dichloromethane, chloroform or dichloroethane, and the base may be triethylamine, pyridine or diisopropylethylamine, and the reaction may be carried out at a temperature in the range of 0 to 40° C. for 1 min to 12 hours.

In Reaction Scheme 2, the compound of formula (I-d), i.e., a compound formula (I) wherein $R_{1a}$ is H and $R_{1b}$ is $OR^a$, $NR^bR^c$ or

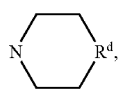

may be prepared by (2a) halogenating the compound of formula (VIII) using a radical halogenating agent, e.g., N-bromosuccinimide (NBS) or N-chlorosuccinimide (NCS), in the presence of a radical initiator such as azobisisobutyronitrile (AIBN) to obtain the compound of formula (IV), and (2b) reacting the compound of formula (IV) with an appropriate amine or alcohol in the presence of an inorganic compound, e.g., $AgNO_3$ or silver (I) triflate.

Reaction (2a) may be conducted in a solvent, e.g., dichloromethane, chloroform or dichloroethane at a temperature in the range of room temperature to the boiling point of the solvent for 1 to 24 hours, and reaction (2b) may be conducted in a solvent, e.g., tetrahydrofuran, methanol or ethanol at a temperature in the range of 10 to 70° C. for 1 to 24 hours.

The compounds of formula (II) and (VIII) used as starting materials in preparing the compounds of formula (I-a), (I-b), (I-c) and (I-d) may be prepared by the method described in Tetrahedron, 1995, 51, 12179; J. Org. Chem., 1993, 58, 4579; J. Chem. Soc., Perkin Trans I., 1992, 2985; Synthesis, 1991, 115&176; J. Med. Chem., 1988, 31, 1316&1754, as shown in Reaction Schemes 3 to 6.

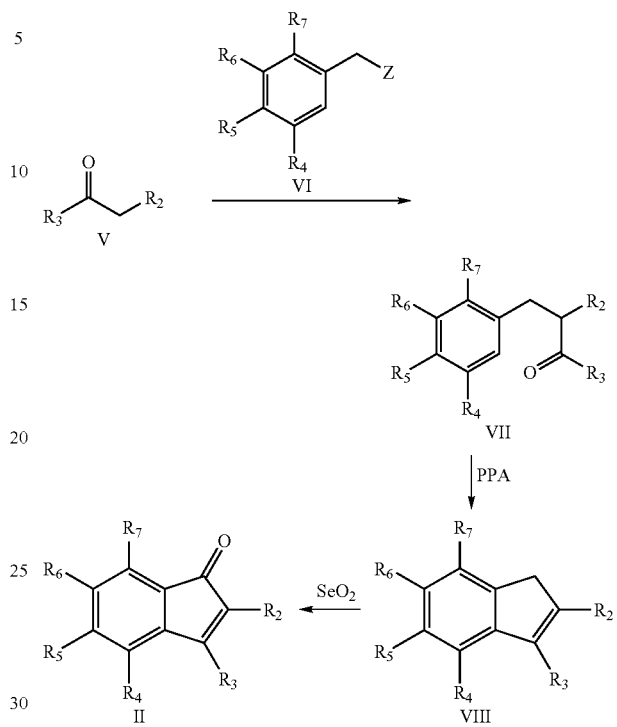

Reaction Scheme 3 wherein, $R_2$, $R_3$, $R_4$, $R_5$, $R_6$ and $R_7$ have the same meanings as defined in formula (I), and Z is halogen or a leaving group such as OMs In Reaction Scheme 3, the compound of formula (II) may be prepared by (3a) reacting the compound of formula (V) with the compound of (VI) in the presence of a base to obtain the corresponding compound of formula (VII), (3b) cyclizing the compound of formula (VII) to form a cyclic compound of formula (VIII), and (3c) oxidizing the compound of formula (VIII).

The solvent which can be used in reaction (3a) includes a polar solvent such as DMF, and the base may be an inorganic base such as $K_2CO_3$, and reaction (3a) may be carried out at 20 to 50° C. for 3 to 15 hours, using the inorganic base in an amount ranging from 2 to 10 equivalents and can be facilitated by the addition of sodium iodide in an amount ranging from 1 to 3 equivalents based on the amount of the compound of formula (V). In reaction (3b), the cyclization of the compound of formula (VII) may be conducted in a solvent, e.g., polyphosphoric acid (PPA), polyphosphoric acid/xylene, methane sulfonic acid (MSA) or pyridinium toluene sulfonate (PPTS) in an amount ranging from 5 to 10 equivalents based on the amount of the compound of formula (VII), at a temperature in the range of 30 to 50° C. for 3 to 12 hours. Further, in reaction (3c), the oxidization of the compound of formula (VIII) may be carried out in a solvent, e.g., 1,4-dioxane or THF, at a temperature in the range of 50 to 120° C. for 7 to 15 hours, using a conventional oxidizing agent, preferably, selenium dioxide in an amount ranging from 5 to 15 equivalents based on the amount of the compound of formula (VIII).

Also, the compounds of formula (V) and (VI) used as starting materials in Reaction Scheme 3 are commercially available or they may be easily prepared in accordance with the conventional procedures disclosed in *Indian J. Chem. Sect. B*, 1983, 22, 830.

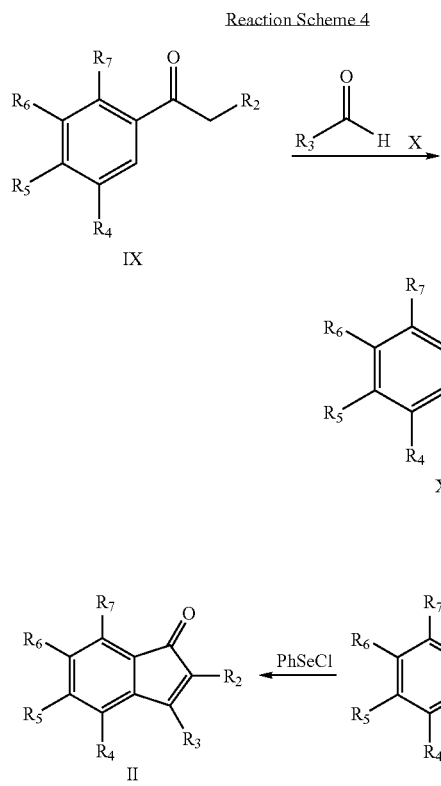

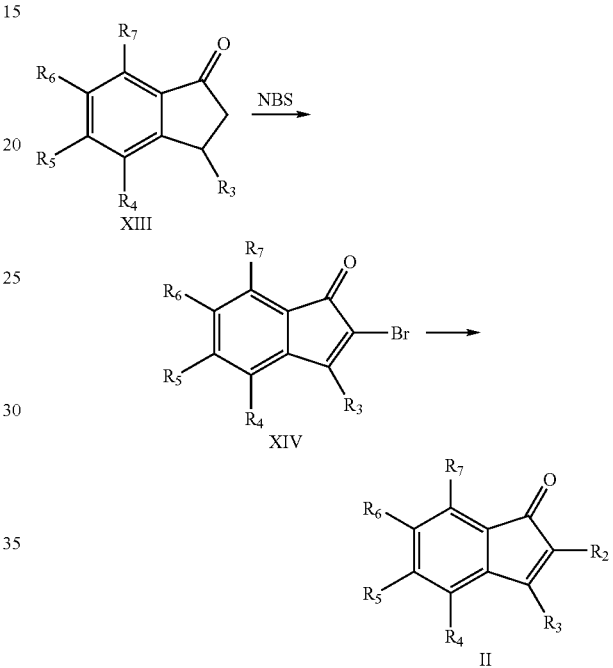

wherein, $R_2$, $R_3$, $R_4$, $R_5$, $R_6$ and $R_7$ have the same meanings as defined in formula (I)

In Reaction Scheme 4, the compound of formula (II) may be prepared by (4a) reacting the compound of formula (IX) with the compound of formula (X) in the presence of a base to obtain the corresponding compound of formula (XI), (4b) cyclizing the compound of formula (XI) to form a cyclic compound of formula (XII), and (4c) oxidizing the compound of formula (XII).

The solvent which can be used in reaction (4a) includes a polar solvent such as DMF, ethanol and nitroethane, and the base may be an inorganic base such as sodium hydroxide, or an organic base such as piperidine, and this condensation reaction (4a) may be carried out at 20 to 80° C. for 3 to 15 hours, using the base in an amount ranging from 2 to 5 equivalents based on the amount of the compound of formula (IX). In reaction (4b), the cyclization of the compound of formula (VII) may be conducted in a solvent, e.g., dichloromethane, chloroform, carbon tetrachloride or xylene, at 20 to 50° C. for about 3 to 12 hours in the presence of methane sulfonic acid (MSA), pyridinium toluene sulfonate (PPTS) or polyphosphoric acid (PPA). In reaction (4a), if the compound of formula (IX) is reacted with the compound of formula (X) in anhydrous nitroethane in the presence of ammonium chloride under a nitrogen gas atmosphere, the above condensation and cyclization reactions (4a) and (4b) may be conducted in one pot to obtain the compound of formula (XII). Further, in reaction (4c), the compound of formula (XII) is oxidized using phenyl selenium chloride and hydrogen peroxide in the presence of an amine such as pyridine, to obtain the compound of formula (II). Phenyl selenium chloride and the amine base may be used in amounts ranging from 1 to 3 equivalents and 1 to 5 equivalents, respectively, based on the amount of the compound of formula (XII), and an excess amount of 30%-hydrogen peroxide may be used in this reaction, which may be carried out in a solvent, e.g., dichloromethane, chloroform, 1,4-dioxane or carbon tetrachloride, at 20 to 70° C. for 3 to 15 hours.

Further, the compounds of formula (IX) and (X) used as starting materials in Reaction Scheme 4 are commercially available.

wherein, $R_2$, $R_3$, $R_4$, $R_5$, $R_6$ and $R_7$ have the same meanings as defined in formula (I).

In Reaction Scheme 5, the compound of formula (II) may be prepared by (5a) bromination of the compound of formula (XIII) to obtain the compound of formula (XIV) and (5b) introducing $R_2$ to the compound of formula (XIV). In reaction (5a), the compound of formula (XIII) is brominated in carbon tetrachloride using NBS in an amount of 1 to 3 equivalents based on the compound of formula (XIII), to obtain the compound of formula (XIV), and the reaction may be conducted at 50 to 100° C. for about 0.5 to 3 hours, while irradiating infrared ray with a lamp or using a radical initiator such as AIBN. Further, in reaction (5b), the compound of formula (II) may be prepared by conducting the conventional palladium-catalyzed C—C coupling reaction, e.g., Suzuki reaction or Heck reaction as described in *Tetrahedron Lett.* 2003, 44, 7095 and *Org. Lett.* 2004, 6, 1577, or by reacting the compound of formula (XIV) with an appropriate $R_2$-containing nucleophile at 70 to 150° C. for 3 to 15 hours in the presence of copper(I) cyanide or sodium methane sulfonate in an amount of 1 to 5 equivalents based on the amount of the compound of formula (XIV) using a polar solvent such as nitroethane and DMF.

Suitable processes for preparing the compound of formula (II) as shown in Reaction Scheme 6 are as follows.

Reaction Scheme 6

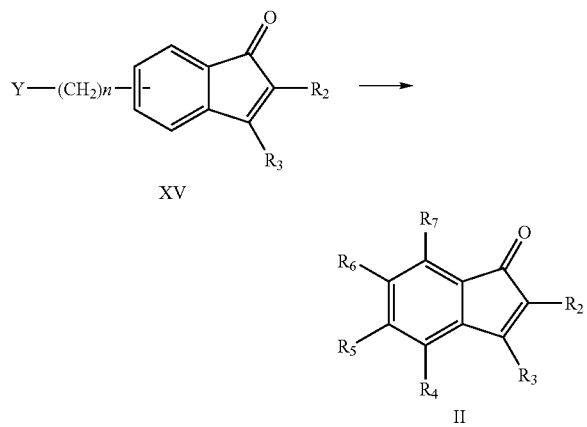

wherein, $R_2$, $R_3$, $R_4$, $R_5$, $R_6$ and $R_7$ have the same meanings as defined in formula (I); Y is OH, SH, $NH_2$, $C_{1-6}$ alkyl or halogen; and n is an integer in the range of 0 to 5.

Method 1): Useful Processes when Y is OH, SH or $NH_2$

The compound of formula (II) may be prepared by conducting conventional acylation or alkylation reactions as described in *J. Org. Chem.* 1988, 53, 3321 and *Tetrahedron Lett.* 2003, 44, 4199.

Specifically, the compound of formula (XV) may be reacted with an appropriate carboxylic acid or an acyl chloride under conventional reaction conditions, using a condensation agent such as dicyclohexyl carbodiimide (DCC) in an amount of about 1 equivalent based on the amount of the compound of formula (XV), to give the compound of formula (II).

The acylation reaction may be conducted in a solvent, e.g., dichloromethane, at room temperature for 1 to 12 hours, when a carboxylic acid is used; and when an acyl chloride is used, the reaction may be conducted at 0 to 30° C. for 1 to 5 hours in the presence of an amine base such as triethylamine.

Alternatively, the compound of formula (II) may be prepared by conducting conventional alkylation reactions, e.g., Mitsunobu reaction as described in *Eur. J. Med. Chem. Chim. Ther.* 2000, 35, 53. Specifically, the compound of formula (XV), an alcohol, triphenyl phosphine and diethyl azodicarboxylate (DEAD) may be dissolved in a solvent, e.g. THF, and stirred at 0 to 30° C. for 3 to 12 hours, to give the compound of formula (II).

In addition, the compound of formula (II) may be prepared by reacting the compound of formula (XV) with an alkyl halide in a solvent, e.g., acetone or N,N-dimethyl formamide at 20 to 100° C. for 3 to 12 hours in the presence of a base such as NaH, $K_2CO_3$ and NaOH.

Method 2): Useful Processes when Y is $C_{1-6}$ Alkyl

The compound of formula (II) may be prepared by conducting a conventional halogenation reaction comprising, e.g., the steps of (6a) reacting the compound of formula (XV) with a radical halogenating agent such as N-bromosuccinimide (NBS) and N-chlorosuccinimide (NCS) in the presence of a radical initiator such as AIBN, to obtain a halogenated intermediate, and (6b) reacting the resulting intermediate with a suitable alkyl, aryl or heterocyclic compound having a substituent selected from the group consisting of OH, $NH_2$, SH and $CO_2H$.

Reaction (6a) may be conducted in a solvent, e.g., carbon tetrachloride, at 50 to 100° C. for 0.5 to 3 hours, and reaction (6b) may be conducted in a solvent, e.g., dichloromethane, THF or DMF, at 0 to 70° C. for 1 to 7 hours, using an inorganic base such as $K_2CO_3$ or an organic base such as triethylamine in an amount ranging from 1 to 3 equivalents based on the amount of the halogenated intermediate obtained in step (6a). Reaction (6b) can be facilitated by the addition of sodium iodide in an amount ranging from 1 to 3 equivalents based on the amount of the halogenated intermediate.

Method 3): Useful Processes when Y is Halogen

The compound of formula (II) may be prepared by conducting conventional palladium-catalyzed C—C coupling reactions, e.g., Suzuki reaction, Heck reaction or Stille reaction as described in Reaction Scheme 5, using the compound of formula (XV) as a starting material.

Exemplary compounds of formula (I) of the present invention which can be prepared in accordance with the methods described above are listed in Table 1:

TABLE 1

| Ex-No. | Structure | $^1$H-NMR (CDCl$_3$, 200 MHz) δ |
|---|---|---|
| 1 | 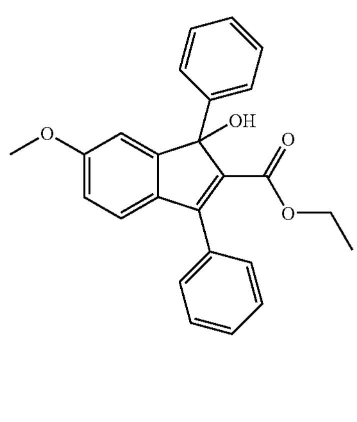 | 7.53-7.46 (m, 5H) 7.31-7.24 (m, 5H) 7.11 (d, J = 8.4 Hz, 1H) 6.85-6.79 (m, 2H) 4.45 (s, 1H) 4.09-3.91 (m, 2H) 3.76 (s, 3H) 0.92 (t, J = 7.2 Hz, 3H) |

TABLE 1-continued

| Ex-No. | Structure | $^1$H-NMR (CDCl$_3$, 200 MHz) δ |
|---|---|---|
| 2 | 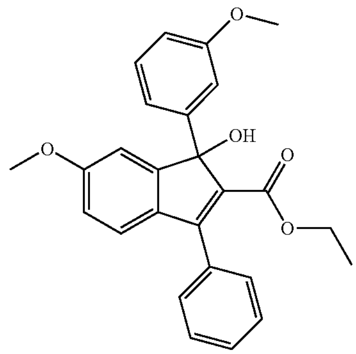 | 7.51-7.46 (m, 5H) 7.26-7.07 (m, 4H) 6.86 (d, J = 2.4 Hz, 1H) 6.78-6.75 (m, 2H) 4.45 (s, 1H) 4.09-3.91 (m, 2H) 3.81 (s, 3H) 3.76 (s, 3H) 1.00 (t, J = 7.2 Hz, 3H) |
| 3 | 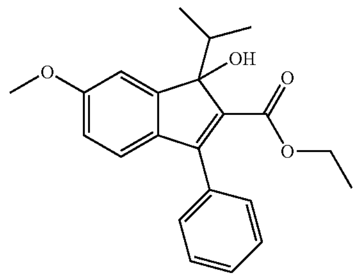 | 7.43-7.34 (m, 5H) 7.26 (s, 3H) 7.02 (d, J = 8.4 Hz, 1H) 6.79 (dd, J = 2.3 Hz, J = 8.4 Hz, 1H) 4.10-4.06 (m, 2H) 3.86 (s, 3H) 2.57 (sept, J = 6.8 Hz, 1H) 1.22 (d, J = 6.8 Hz, 3H) 1.00 (t, J = 7.2 Hz, 3H) 0.69 (t, J = 6.8 Hz, 3H) |
| 4 | 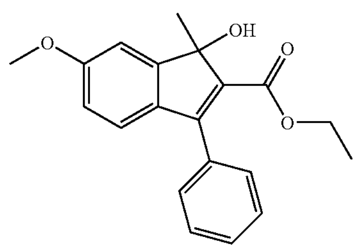 | 7.44~6.79(m, 8H), 4.10(q, J = 7.2 Hz, 2H), 3.88(s, 3H), 1.78(s, 3H), 1.06(t, J = 7.2 Hz, 3H) |
| 5 | 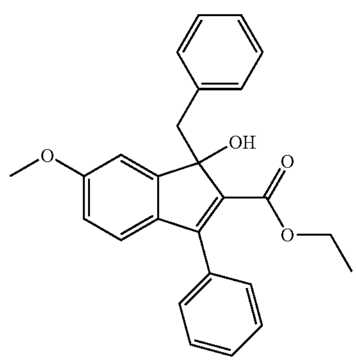 | 7.35~6.77(m, 13H), 4.13(q, J = 7.2 Hz, 2H), 4.05(s, 1H), 3.85(s, 3H), 3.48(s, 2H), 1.05(t, J = 7.2 Hz, 3H) |
| 6 | 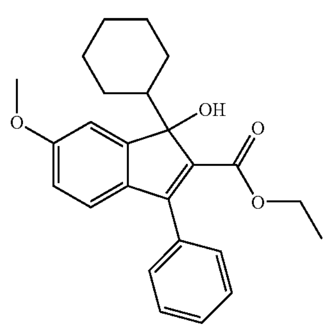 | 7.51~6.75(m, 8H), 4.12~4.02(m, 2H), 3.94(s, 1H), 3.86(s, 3H), 2.17~1.08(m, 10H), 1.00(t, J = 7.2 Hz, 3H) |

TABLE 1-continued

| Ex-No. | Structure | $^1$H-NMR (CDCl$_3$, 200 MHz) δ |
|---|---|---|
| 7 | 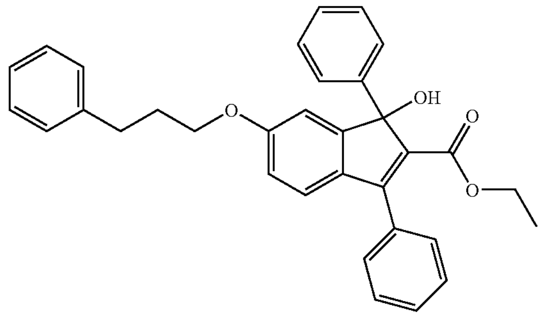 | 7.63~6.73(m, 18H), 4.47(s, 1H), 4.11(q, J = 7.2 Hz, 2H), 4.07~3.88(m, 2H), 2.75(t, J = 7.6 Hz, 2H), 2.07~2.00(m, 2H), 0.93(t, J = 7.2 Hz, 3H) |
| 8 | 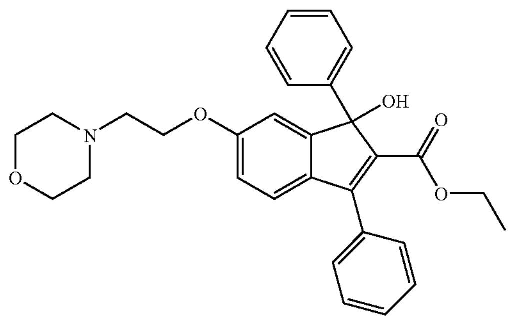 | 7.68~6.75(m, 13H), 4.43(s, 1H), 4.04~4.00(q, J = 7.2 Hz, 2H), 4.01~3.93(m, 2H), 3.69(t, J = 4.9 Hz, 4H), 2.73(t, J = 5.1 Hz, 2H), 2.51(t, J = 4.9 Hz, 4H), 0.92(t, J = 7.2 Hz, 3H); mp 121-123° C. |
| 9 | 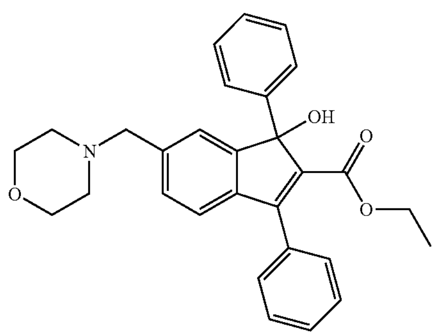 | 7.60-7.06 (m, 13H) 3.95-4.05 (m, 2H) 3.60-3.80 (m, 4H) 3.45 (s, 2H) 2.30-2.43 (m, 4H) 0.92 (t, J = 7.3 Hz, 3H) |
| 10 | 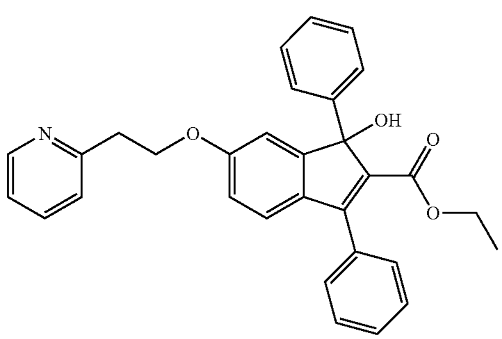 | 8.53-8.49 (m, 1H) 7.59-7.51 (m, 6H) 7.48-7.06 (m, 8H) 6.85-6.74 (m, 2H) 4.35-4.27 (m, 2H) 4.00-3.92 (m, 2H) 3.19 (t, J = 6.5 Hz, 2H) 0.92 (t, J = 7.3 Hz, 3H) |

TABLE 1-continued

| Ex-No. | Structure | $^1$H-NMR (CDCl$_3$, 200 MHz) δ |
|---|---|---|
| 11 | 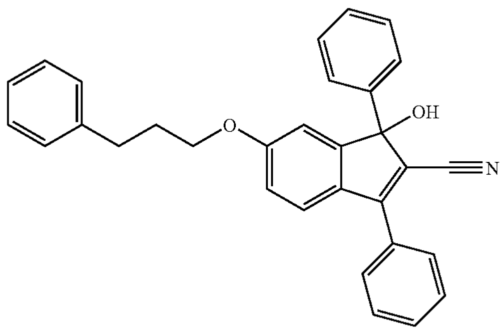 | 7.70-6.90 (m, 18H) 3.95 (t, J = 6.2 Hz, 2H) 2.77 (t, J = 7.4 Hz, 2H) 2.10-2.04 (m, 2H) |
| 12 | 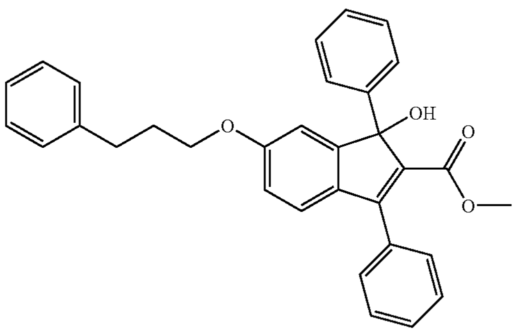 | 7.50~6.72(m, 18H), 4,01(t, J = 6.0 Hz, 2H), 3.52(s, 3H), 2.75(t, J = 7.2 Hz, 2H), 2.10-2.04(m, 2H) |
| 13 | 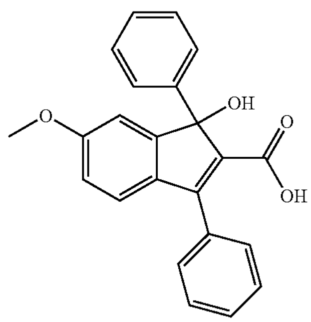 | 7.46~6.73(m, 13H), 3.75(s, 3H) |
| 14 | 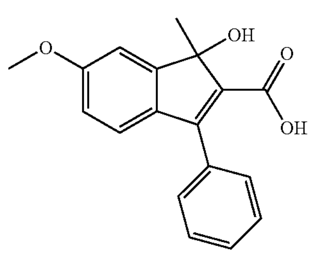 | 7.45~6.80(m, 8H), 3.88(s, 3H), 1.78(s, 3H) |
| 15 | 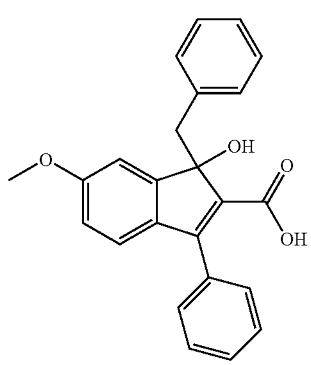 | 7.39~6.78(m, 13H), 3.87(s, 3H), 3.50(s, 2H) |

TABLE 1-continued

| Ex-No. | Structure | $^1$H-NMR (CDCl$_3$, 200 MHz) δ |
|---|---|---|
| 16 | 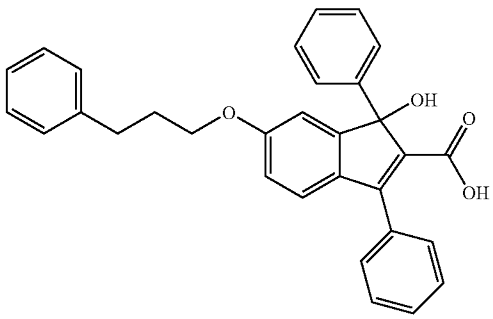 | 7.45~6.77(m, 18H), 4.05~3.87(m, 2H), 2.76(t, J = 7.4 Hz, 2H), 2.06~2.01(m, 2H) |
| 17 | 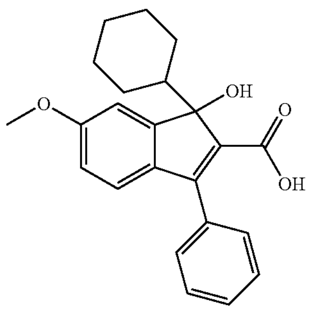 | 7.53~6.77(m, 8H), 3.86(s, 1H), 2.23~0.88(m, 11H) |
| 18 | 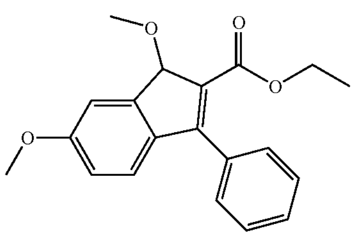 | 7.51-7.41 (m, 5H) 7.17 (d, J = 2.4 Hz, 1H) 7.10 (d, J = 8.4 Hz, 1H) 6.83 (dd, J = 8.4, 2.4 Hz, 1H) 5.48 (s, 1H) 4.22-4.09 (m, 2H) 3.87 (s, 3H) 3.30 (s, 3H) 1.12 (t, J = 7.2 Hz, 3H) |
| 19 | 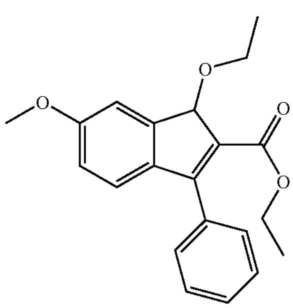 | 7.51-7.42 (m, 5H) 7.16 (s, 1H) 7,08 (d, J = 8.3 Hz, 1H) 7.82 (dd, J = 8.3, 2.3 Hz, 1H) 5.49 (s, 1H) 4.24-4.07 (m, 2H) 3.86 (s, 3H) 3.64-3.49 (m, 2H) 1.22 (t, J = 7.0 Hz, 3H) 1.13 (t, J = 7.1 Hz, 3H) |
| 20 | 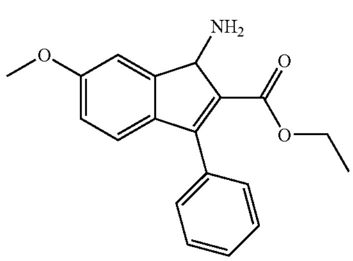 | 7.22-7.06 (m, 6H) 6.92-6.86 (m, 2H) 6.04 (brs, NH$_2$) 4.72 (s, 1H) 4.11-4.03 (m, 2H) 3.84 (s, 3H) 1.05 (t, J = 7.2 Hz, 3H) |

TABLE 1-continued

| Ex-No. | Structure | ¹H-NMR (CDCl₃, 200 MHz) δ |
|---|---|---|
| 21 | 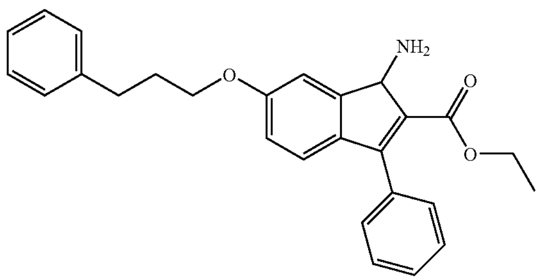 | 7.29-7.04 (m, 11H) 7.04-6.85 (m, 2H) 6.01 (brs, 2H) 4.71 (s, 1H) 4.12-3.95 (m, 4H) 2.81 (t, J = 7.2 Hz, 2H) 2.11 (qujnt, J = 7.2 Hz, 2H) 1.05 (t, J = 7.2 Hz, 3H) |
| 22 | 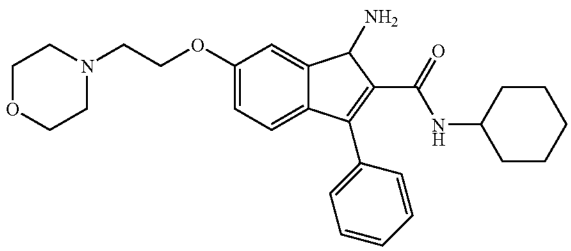 | 7.32-7.16 (m, 5H) 7.01 (d, J = 8.3 Hz, 1H) 6.92 (d, J = 2.2 Hz, 1H) 6.82 (dd, J = 2.2 8.3 Hz, 1H) 6.25 (brs, 2H) 4.54 (s, 1H) 4.10-4.20 (m, 3H) 3.74 (t, J = 4.6 Hz, 4H) 2.81 (t, J = 5.7 Hz, 3H) 2.54 (t, J = 4.6 Hz, 4H) 0.70-1.46 (m, 10H) |
| 23 | 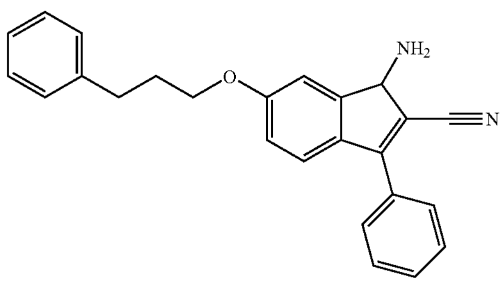 | 7.34-7.09 (m, 11H) 6.93-6.83 (m, 2H) 4.89 (s, 2H) 3.99 (t, J = 6.5 Hz, 2H) 2.82 (t, J = 6.5 Hz, H) 2.10 (qujnt, J = 6.5 Hz, 2H) |
| 24 | 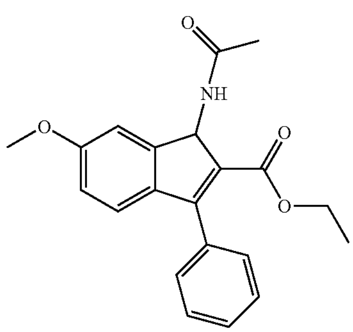 | 10.47 (brs, 1H) 7.86 (d, J = 2.4 Hz, 1H) 7.24-7.17 (m, 3H) 7.04-7.01 (m, 3H) 6.89 (dd, J = 8.4, 2.4 Hz, 1H) 4.72 (s, 1H) 4.13-4.01 (m, 2H) 3.85 (s, 3H) 2.32 (s, 3H) 1.04 (t, J = 7.2 Hz, 3H) |
| 25 | 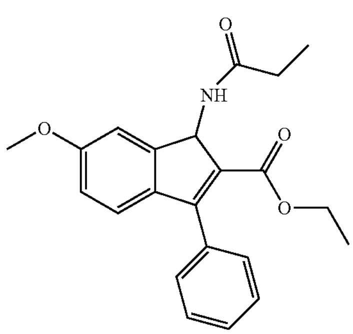 | 10.52 (brs, 1H) 7.92 (d, J = 2.2 Hz, 1H) 7.21-7.16 (m, 3H) 7.04-7.00 (m, 3H) 6.88 (dd, J = 8.1, 2.4 Hz, 1H) 4.71 (s, 1H) 4.11-4.02 (m, 2H) 3.85 (s, 3H) 2.58 (q, J = 15.1, 7.5 Hz, 2H) 1.34 (t, J = 7.4 Hz, 3H) 1.04 (t, J = 7.1 Hz, 3H) |

TABLE 1-continued

| Ex-No. | Structure | $^1$H-NMR (CDCl$_3$, 200 MHz) δ |
|---|---|---|
| 26 | 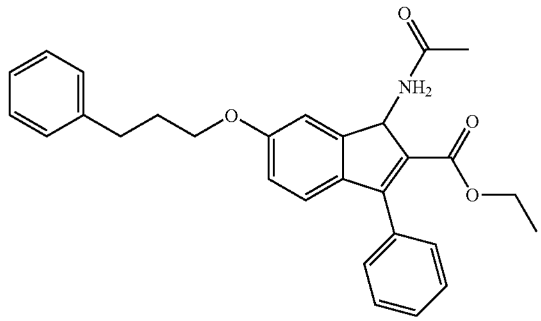 | 10.45 (brs, 1H) 7.85 (d, J = 2.4 Hz, 1H) 7.31-7.17 (m, 10H) 7.02 (d, J = 8.4 Hz, 1H) 6.89 (dd, J = 2.4, 8.4 Hz, 1H) 4.71 (s, 1H) 4.12-3.99 (m, 4H) 2.82 (t, J = 7.2 Hz, 2H) 2.33 (s, 3H) 2.11 (qujnt, J = 7.2 Hz, 2H) 1.04 (t, J = 7.2 Hz, 3H) |
| 27 | 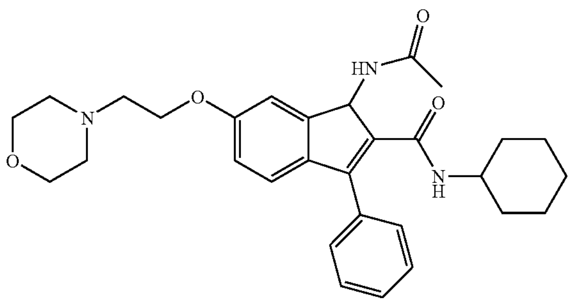 | 11.62 (s, 1H) 7.88 (d, J = 2.4 Hz, 1H) 7.33-7.26 (m, 5H) 7.15 (d, J = 7.4 Hz, 1H) 6.97-6.83 (m, 1H) 5.29 (d, 6.82 J = 6.0 Hz, 1H) 4.10-4.20 (m, 3H) 3.68-3.65 (m, 4H) 2.81 (t, J = 5.7 Hz, 2H) 2.54-2.59 (m, 4H) 2.31 (s, 3H) 0.70-1.46 (m, 10H) |
| 28 | 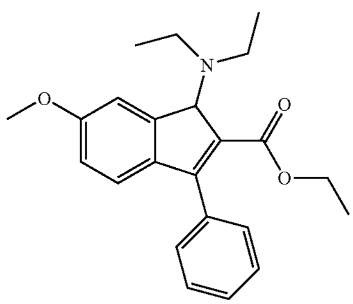 | 7.45-7.00 (m, 7H) 6.80 (dd, J = 8.4, 2.4 Hz, 1H) 4.77 (s, 1H) 4.02-3.92 (m, 2H) 3.83 (s, 3H) 3.60 (q, J = 14.4, 7.2 Hz, 4H) 1.20 (t, J = 6.9 Hz, 6H) 0.98 (t, J = 7.2 Hz, 3H) |
| 29 | 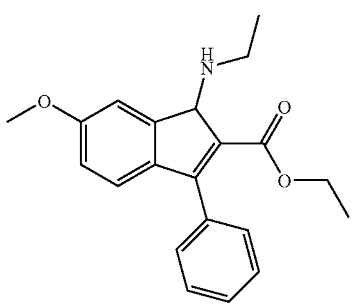 | 7.35 (d, J = 2.1 Hz, 1H) 7.21-7.06 (m, 6H) 6.86 (dd, J = 8.4, 2.4 Hz, 1H) 4.68 (s, 1H) 4.07-3.94 (m, 4H) 3.83 (s, 3H) 1.42 (t, J = 7.2 Hz, 3H) 1.00 (t, J = 7.2 Hz, 3H) |
| 30 | 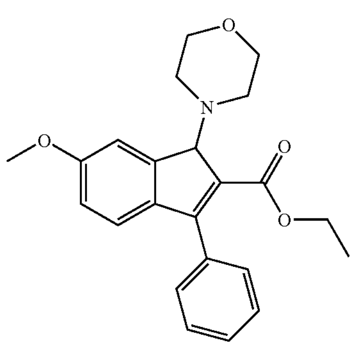 | 7.21-7.02 (m, 7H) 6.82 (dd, J = 8.4, 2.4 Hz, 1H) 4.77 (s, 1H) 4.00-3.90 (m, 6H) 3.82 (s, 3H) 3.73-3.65 (m, 2H) 3.57-3.52 (m, 2H) 0.97 (t, J = 7.2 Hz, 3H) |

TABLE 1-continued

| Ex-No. | Structure | $^1$H-NMR (CDCl$_3$, 200 MHz) δ |
|---|---|---|
| 31 | 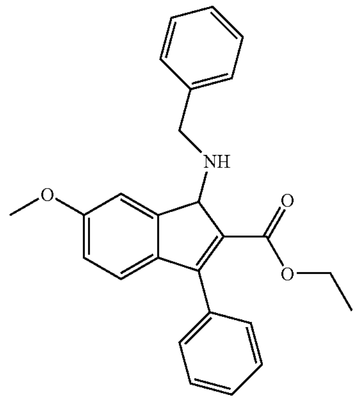 | 8.37 (brs, 1H) 7.44-7.14 (m, 12H) 7.05 (d, J = 8.7 Hz, 1H) 5.00 (d, J = 6.3 Hz, 2H) 4.70 (s, 1H) 4.04-3.98 (m, 2H) 3.64 (s, 3H) 1.00 (t, J = 7.2 Hz, 3H) |
| 32 | 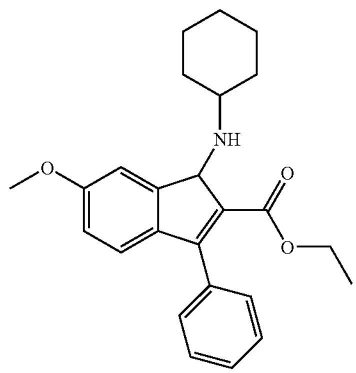 | 7.21-7.05 (m, 7H) 7.86 (dd, J = 8.4, 2.1 Hz, 1H) 4.66 (s, 1H) 4.07-3.96 (m, 3H) 3.83 (s, 3H) 2.21-2.13 (m, 2H) 1.88-1.83 (m, 2H) 1.69-1.26 (m, 6H) 1.00 (t, J = 7.2 Hz, 3H) |

The above compounds of the present invention are as follows:
1) 1-hydroxy-6-methoxy-1,3-diphenyl-1H-indene-2-carboxylic acid ethyl ester
2) 1-hydroxy-6-methoxy-1-(3-methoxy-phenyl)-3-phenyl-1H-indene-2-carboxylic acid ethyl ester
3) 1-hydroxy-1-isopropyl-6-methoxy-3-phenyl-1H-indene-2-carboxylic acid ethyl ester
4) 1-hydroxy-6-methoxy-1-methyl-3-phenyl-1H-indene-2-carboxylic acid ethyl ester
5) 1-benzyl-1-hydroxy-6-methoxy-3-phenyl-1H-indene-2-carboxylic acid ethyl ester
6) 1-cyclohexyl-1-hydroxy-6-methoxy-3-phenyl-1H-indene-2-carboxylic acid ethyl ester
7) 1-hydroxy-1,3-diphenyl-6-(3-phenyl-propoxy)-1H-indene-2-carboxylic acid ethyl ester
8) 1-hydroxy-6-(2-morpholine-4-yl-ethoxy)-1,3-diphenyl-1H-indene-2-carboxylic acid ethyl ester
9) 1-hydroxy-6-morpholine-4-yl-methyl-1,3-diphenyl-1H-indene-2-carboxylic acid ethyl ester
10) 1-hydroxy-1,3-diphenyl-6-(2-pyridine-2-yl-ethoxy)-1H-indene-2-carboxylic acid ethyl ester
11) 1-hydroxy-1,3-diphenyl-6-(3-phenyl-propoxy)-1H-indene-2-carbonitrile
12) 1-hydroxy-1,3-diphenyl-6-(3-phenyl-propoxy)-1H-indene-2-carboxylic acid methyl ester
13) 1-hydroxy-6-methoxy-1,3-diphenyl-1H-indene-2-carboxylic acid
14) 1-hydroxy-6-methoxy-1-methyl-3-phenyl-1H-indene-2-carboxylic acid
15) 1-benzyl-1-hydroxy-6-methoxy-3-phenyl-1H-indene-2-carboxylic acid
16) 1-hydroxy-1,3-diphenyl-6-(3-phenyl-propoxy)-1H-indene-carboxylic acid
17) 1-cyclohexyl-1-hydroxy-6-methoxy-3-phenyl-1H-indene-2-carboxylic acid
18) 1,6-dimethoxy-3-phenyl-1H-indene-2-carboxylic acid ethyl ester
19) 1-ethoxy-6-methoxy-3-phenyl-1H-indene-2-carboxylic acid ethyl ester
20) 1-amino-6-methoxy-3-phenyl-1H-indene-2-carboxylic acid ethyl ester
21) 1-amino-3-phenyl-6-(3-phenyl-propoxy)-1H-indene-2-carboxylic acid ethyl ester
22) 1-amino-6-(2-morpholin-4-yl-ethoxy)-3-phenyl-1H-indene-2-carboxylic acid cyclohexyl amide
23) 1-amino-3-phenyl-6-(3-phenyl-propoxy)-1H-indene-2-carbonitrile
24) 1-acetylamino-6-methoxy-3-phenyl-1H-indene-2-carboxylic acid ethyl ester
25) 6-methoxy-3-phenyl-1-propionylamino-1H-indene-2-carboxylic acid ethyl ester
26) 1-acetylamino-3-phenyl-6-(3-phenyl-propoxy)-1H-indene-2-carboxylic acid ethyl ester
27) 1-acetylamino-6-(2-morpholin-4-yl-ethoxy)-3-phenyl-1H-indene-2-carboxylic acid cyclohexyl amide
28) 1-diethylamino-6-methoxy-3-phenyl-1H-indene-2-carboxylic acid ethyl ester
29) 1-ethylamino-6-methoxy-3-phenyl-1H-indene-2-carboxylic acid ethyl ester 30) 6-methoxy-1-morpholin-4-yl-3-phenyl-1H-indene-2-carboxylic acid ethyl ester
31) 1-benzyl amino-6-methoxy-3-phenyl-1H-indene-2-carboxylic acid ethyl ester
32) 1-cyclohexyl amino-6-methoxy-3-phenyl-1H-indene-2-carboxylic acid ethyl ester The inventive indene derivative of formula (I) and a pharmaceutically acceptable salt thereof is capable of selectively modulating activities of PPARs, and thus it causes no adverse side effects such as weight gain, cardiac hypertrophy, edema and liver damage.

The present invention also includes within its scope a pharmaceutical composition comprising a therapeutically effective amount of the novel compounds of formula (I), as defined above, or a pharmaceutically acceptable salt thereof as an active ingredient together with a pharmaceutically acceptable carrier.

The inventive pharmaceutical composition is useful for the treatment and prevention of disorders modulated by PPARs, i.e., metabolic syndromes such as diabetes, obesity, arteriosclerosis, hyperlipidemia, hyperinsulinism and hypertension; inflammatory diseases such as osteoporosis, liver cirrhosis and asthma; and cancer.

The pharmaceutical compositions of the invention may be formulated for administration orally or parenterally, including intravenous, intraperitoneal, subcutaneous, rectal and topical routes of administration. The composition for oral administration may take various forms such as tablets, soft and hard gelatin capsules, aqueous solutions, suspensions, emulsions, syrups, granules and elixirs, which may contain conventional additives such as a diluent (e.g., lactose, dextrose, sucrose, mannitol, sorbitol, cellulose and glycine), a lubricant (e.g., silica, talc, stearic acid or its magnesium and calcium salts and polyethylene glycol). In the case of the tablet form, the composition may further comprise a binder (e.g., magnesium aluminum silicate, starch paste, gelatin, tragacanth, methyl cellulose, sodium carboxymethyl cellulose and polyvinyl pyrrolidone) and optionally a disintegrant (e.g., starch, agar and alginic acid or its sodium salt), absorbent, colorant, flavor, sweetener and the like.

The composition may be sterilized and/or contain an adjuvant such as a preservative, stabilizer, wetting agent, emulsifier, a salt for controlling an osmotic pressure and/or a buffer solution, and other pharmaceutically effective materials.

The inventive compounds may be administered as an active ingredient in an effective amount ranging from about 0.1 to 500 mg/kg, preferably from about 0.5 to 100 mg/kg per day in a single dose or in divided doses.

The following Preparations and Examples are given for the purpose of illustration only and are not intended to limit the scope of the invention.

PREPARATION EXAMPLE 1

Preparation of
6-methoxy-3-phenyl-1H-indene-2-carboxylic Acid
Ethyl Ester

Step 1) Preparation of 2-(3-methoxy-benzyl)-3-oxo-3-phenyl-propionic Acid Ethyl Ester Ethylbenzoyl acetate (7 g, 36.42 mmol), potassium carbonate (15.1 g, 109.26 mmol) and sodium iodide (6.55 g, 43.70 mmol) were dissolved in N,N-dimethyl formamide and the mixture was stirred at room temperature. 3-Methoxybenzyl chloride (6.274 g, 40.06 mmol) was added thereto followed by stirring for 1 hr at room temperature. The resulting mixture washed with saturated ammonium chloride and extracted with ethyl acetate. The organic layer was separated, dried over anhydrous $MgSO_4$ and concentrated under a reduced pressure. The resulting residue was purified by flash chromatography to obtain 10.69 g of the titled compound.

$^1$H-NMR (200 MHz, $CDCl_3$) δ 7.96 (dd, J=6.8 Hz, J=7.2 Hz, 2H), 7.56 (m, 1H) 7.24 (d, J=10.6 Hz, 1H), 6.84~6.69 (m, 3H), 4.63 (t, J=7.3 Hz, 1H), 4.16~4.06 (m, 2H), 3.76 (s, 3H), 3.31 (d, J=6.8 Hz, 2H), 1.13 (t, J=7.1 Hz, 3H)

Step 2) Preparation of
6-methoxy-3-phenyl-1H-indene-2-carboxylic Acid
Ethyl Ester The compound (10.69 g, 34.26 mmol) obtained in Step 1 was mixed with 100 g of poly phosphoric acid, and stirred for 1 hr at 30~45° C. The resulting dark mud-color solution washed with water and extracted with ethyl acetate. The organic layer was separated, dried over anhydrous $MgSO_4$ and concentrated under a reduced pressure. The resulting residue was purified by flash chromatography to obtain 4.064 g of the titled compound (yield: 40%) as a white solid.

$^1$H-NMR (200 MHz, $CDCl_3$) δ 7.46~7.40 (m, 5H), 7.20 (q, J=10.8 Hz, 2H), 6.87 (dd, 8.6 Hz, J=2.3 Hz, 1H), 4.13 (q, J=7.2 Hz, 2H), 3.86 (s, 3H), 3.82 (s, 2H), 1.14 (t, 7.1 Hz, 3H)

PREPARATION EXAMPLE 2

Preparation of
6-hydroxy-1-oxo-3-phenyl-1H-indene-2-carboxylic
Acid Ethyl Ester

Step 1) Preparation of 2-(3-hydroxy-benzyl)-3-oxo-3-phenyl-propionic Acid Ethyl Ester Ethylbenzoyl acetate (27.6 g, 161.28 mmol), potassium carbonate (44.58 g, 322.56 mmol) and sodium iodide (29 g, 193.53 mmol) were dissolved in N,N-dimethyl formamide and the mixture was stirred for 1 hr at room temperature. 3-Chloromethylphenol (27.6 g, 193.538 mmol) was added thereto followed by stirring for 5 hrs at room temperature. The resulting mixture washed with saturated ammonium chloride and extracted with ethyl acetate. The organic layer was separated, dried over anhydrous $MgSO_4$ and concentrated under a reduced pressure. The resulting residue was purified by flash chromatography to obtain 46.51 mg of the titled compound (yield: 96%).

$^1$H-NMR (200 MHz, $CDCl_3$) δ 7.99~7.94 (m, 2H), 7.60~7.40 (m, 3H) 7.23 (m, 1H), 6.79~6.67 (m, 3H), 4.65 (m 1H), 4.20~4.05 (m, 2H), 3.28 (d, J=7.4 Hz, 2H), 1.17~1.08 (m, 3H)

Step 2) Preparation of
6-hydroxy-3-phenyl-1H-indene-2-carboxylic Acid
Ethyl Ester The compound (10 g, 33.51 mmol) obtained in Step 1 was mixed with poly phosphoric acid (10 g), and stirred for 2 hrs at room temperature. The resulting bright yellow solution washed with water and extracted with ethyl acetate. The organic layer was separated, dried over anhydrous $MgSO_4$ and concentrated under a reduced pressure to obtain a residue. Such a procedure was repeated seven times and residues obtained therefrom were combined and purified by flash chromatography to obtain 29.7 g of the titled compound as a light yellow solid.

$^1$H-NMR (200 MHz, CDCl$_3$) δ 7.45~7.39 (m, 5H), 7.26 (d, J=0.8 Hz, 1H), 7.02 (t, J=0.9 Hz, 1H), 6.77 (dd, J=8.2 Hz, J=2.4 Hz, 1H), 5.30 (s, 1H), 4.13 (q, J=7.2 Hz, 2H), 3.81 (s, 1H), 1.13 (t, J=7.1 Hz, 3H)

Step 3) Preparation of 6-hydroxy-1-oxo-3-phenyl-1H-indene-2-carboxylic Acid Ethyl Ester The compound (16.00 g, 57.07 mmol) obtained in Step 2 was dissolved in 1,4-dioxane. Selenium dioxide (63.33 g, 570.07 mmol) was added thereto and refluxed for 10 hrs, followed by cooling. The resulting mixture washed with 1M sodium bicarbonate, and successively extracted with diethyl ether. The organic layer was separated, dried over anhydrous MgSO$_4$, and concentrated under a reduced pressure. The resulting residue was purified by flash chromatography to obtain 10.198 g of the titled compound (yield: 61%) as a red solid.

$^1$H-NMR (200 MHz, CDCl$_3$) δ 7.44~7.38 (m, 5H), 7.12 (d, J=8.4 Hz, 1H), 7.02 (d, J=2.0 Hz, 1H), 6.76 (dd, J=8.4, 2.0 Hz, 1H), 4.12 (q, J=7.1 Hz, 2H), 3.80 (s, 2H), 1.12 (t, J=7.1 Hz, 3H)

Example 1

Preparation of 1-hydroxy-6-methoxy-1,3-diphenyl-1H-indene-2-carboxylic Acid Ethyl Ester

Step 1) Preparation of 6-methoxy-1-oxo-3-phenyl-1H-indene-2-carboxylic Acid Ethyl Ester 6-Methoxy-3-phenyl-1H-indene-2-carboxylic acid ethyl ester (1 g, 3.39 mmol) prepared in Preparation Example 1 was dissolved in 1,4-dioxane and selenium dioxide (5.65 g, 50.96 mmol) was added thereto. The mixture was refluxed for 24 hrs, cooled, washed with 1M sodium bicarbonate, and extracted with diethyl ether. The organic layer was separated, dried over anhydrous MgSO$_4$, and concentrated under a reduced pressure. The resulting residue was purified by flash chromatography to obtain 756 mg of the titled compound (yield: 72%) as a red solid.

$^1$H-NMR (200 MHz, CDCl$_3$) δ 7.51 (s, 5H), 7.19 (d, J=2.4 Hz, 1H), 7.08 (d, J=8.2 Hz, 1H), 6.83 (dd, J=8.0 Hz, J=2.2 Hz, 1H), 4.18 (q, J=7.1 Hz, 2H), 3.86 (s, 3H), 1.15 (t, J=7.1 Hz, 3H)

Step 2) Preparation of 1-hydroxy-6-methoxy-1,3-diphenyl-1H-indene-2-carboxylic Acid Ethyl Ester The compound (300 mg, 0.97 mmol) obtained in Step 1 was dissolved in THF and 1.5 equivalents of phenylmagnesium chloride were added thereto, followed by stirring for 1 hr at 0° C. Then, the resulting mixture washed with saturated saline, and extracted with ethyl acetate. The organic layer was separated, dried over anhydrous MgSO$_4$, and concentrated under a reduced pressure. The resulting residue was purified by flash chromatography to obtain 285 mg of the titled compound (yield: 76%).

Example 2

Preparation of 1-hydroxy-6-methoxy-1-(3-methoxyphenyl)-3-phenyl-1H-indene-2-carboxylic Acid Ethyl Ester 6-Methoxy-1-oxo-3-phenyl-1H-indene-2-carboxylic acid ethyl ester (100 mg, 0.325 mmol) obtained in Example 1 was dissolved in THF and 1.5 equivalents of 3-methoxyphenylmagnesium bromide were added thereto, followed by stirring for 1 hr at 0° C. Then, the reaction mixture washed with saturated saline and extracted with ethyl acetate. The organic layer was separated, dried over anhydrous MgSO$_4$, and concentrated under a reduced pressure. The resulting residue was purified by flash chromatography to obtain 122 mg of the titled compound (yield: 90.4%).

Example 3

Preparation of 1-hydroxy-isopropyl-6-methoxy-3-phenyl-1H-indene-2-carboxylic Acid Ethyl Ester 6-Methoxy-1-oxo-3-phenyl-1H-indene-2-carboxylic acid ethyl ester (300 mg, 0.974 mmol) obtained in Example 1 was dissolved in THF and 1.5 equivalents of isopropylmagnesium chloride were added thereto, followed by stirring for 1 hr at 0° C. The resulting mixture washed with saturated saline and extracted with ethyl acetate. The organic layer was separated, dried over anhydrous MgSO$_4$, and concentrated under a reduced pressure. Then, the resulting residue was purified by flash chromatography to obtain 155 mg of the titled compound (yield: 45.2%).

Example 4

Preparation of 1-hydroxy-6-methoxy-1-methyl-3-phenyl-1H-indene-2-carboxylic acid ethyl ester 6-Methoxy-1-oxo-3-phenyl-1H-indene-2-carboxylic acid ethyl ester (300 mg, 0.974 mmol) obtained in Example 1 was dissolved in THF and 1.2 equivalents of methylmagnesium chloride were added thereto, followed by stirring for 3 hrs at 0° C. The resulting mixture washed with saturated saline and extracted with ethyl acetate. The organic layer was separated, dried over anhydrous MgSO$_4$, and concentrated under a reduced pressure. The resulting residue was purified by flash chromatography to obtain 126 mg of the titled compound (yield: 38%).

Example 5

Preparation of 1-benzyl-1-hydroxy-6-methoxy-3-phenyl-1H-indene-2-carboxylic Acid Ethyl Ester 6-Methoxy-1-oxo-3-phenyl-1H-indene-2-carboxylic acid ethyl ester (300 mg, 0.974 mmol) obtained in Example 1 was dissolved in THF and 1.2 equivalents of benzylmagnesium chloride were added thereto, followed by stirring for 3 hrs at 0° C. The resulting mixture washed with saturated saline and extracted with ethyl acetate. The organic layer was separated, dried over anhydrous MgSO$_4$, and concentrated under a reduced pressure. The resulting residue was purified by flash chromatography to obtain 50 mg of the titled compound (yield: 13%).

Example 6

Preparation of 1-cyclohexyl-1-hydroxy-6-methoxy-3-phenyl-1H-indene-2-carboxylic Acid Ethyl Ester 6-Methoxy-1-oxo-3-phenyl-1H-indene-2-carboxylic acid ethyl ester (78 mg, 0.253 mmol) obtained in Example 1 was dissolved in THF, and 18%-cyclohexylmagnesium chloride (0.7 mL, 0.506 mmol) was added thereto, followed by stirring for 5 hrs at 0° C. The resulting mixture washed with saturated saline and extracted with ethyl acetate. The organic layer was separated, dried over anhydrous MgSO$_4$, and concentrated under a reduced pressure. The resulting residue was purified by flash chromatography to obtain 30 mg of the titled compound (yield: 30%).

Example 7

Preparation of 1-hydroxy-1,3-diphenyl-6-(3-phenyl-propoxy)-1H-indene-2-carboxylic Acid Ethyl Ester Step 1) Preparation of 1-oxo-3-phenyl-6-(3-phenyl-propoxy)-1H-indene-2-carboxylic Acid Ethyl Ester 6-Hydroxy-1-oxo-3-phenyl-1H-indene-2-carboxylic acid ethyl ester (2 g, 6.79 mmol) prepared in Preparation Example 2, potassium carbonate (1.40 g, 10.19 mmol) and sodium iodide (0.2 g, 1.39 mmol) were dissolved in N,N-dimethyl formamide, and 1-bromo-3-phenyl propane (2.066 ml, 13.592 mmol) was added thereto, followed by stirring for 8 hrs at room temperature. The resulting mixture washed with saturated ammonium chloride and extracted with ethyl acetate. The organic layer was separated, dried over anhydrous MgSO$_4$, and concentrated under a reduced pressure. Then, the resulting residue was purified by flash chromatography to obtain 2.37 g of the titled compound (yield: 85%) as a dark red solid.

$^1$H-NMR (200 MHz, CDCl$_3$) δ 7.56 (d, J=9 Hz, 5H), 7.36~7.21 (m, 6H), 7.09 (d, J=8.2 Hz, 1H), 6.83 (dd, J=8.0 Hz, J=2.4 Hz, 1H), 4.26~4.16 (m, 2H), 4.03 (t, J=6.3 Hz, 2H), 2.98~2.80 (m, 2H), 2.22~2.07 (m, 2H), 1.63~1.15 (m, 3H)

Step 2) Preparation of 1-hydroxy-1,3-diphenyl-6-(3-phenyl-propoxy)-1H-indene-2-carboxylic Acid Ethyl Ester 1-Oxo-3-phenyl-6-(3-phenyl-propoxy)-1H-indene-2-carboxylic acid ethyl ester (350 mg, 0.85 mmol) obtained in Step 1 was dissolved in THF, and phenylmagnesium chloride (0.064 mL, 0.93 mmol) was added thereto, followed by stirring for 1 hr at 0° C. The resulting mixture washed with saturated saline and extracted with ethyl acetate. The organic layer was separated, dried over anhydrous MgSO$_4$, and concentrated under a reduced pressure. The resulting residue was purified by flash chromatography to obtain 475 mg of the titled compound (yield: 100%).

Example 8

Preparation of 1-hydroxy-6-(2-morpholine-4-yl-ethoxy)-1,3-diphenyl-1H-indene-2-carboxylic Acid Ethyl Ester Step 1) Preparation of 6-(2-morpholine-4-ylethoxy)-1-oxo-3-phenyl-1H-indene-2-carboxylic Acid Ethyl Ester 6-Hydroxy-1-oxo-3-phenyl-1H-indene-2-carboxylic acid ethyl ester (2 g, 6.79 mmol) prepared in Preparation Example 2 was dissolved in THF/benzene (270 mL/90 mL) solution, and 2-hydroxyethylmorpholine (5.83 g, 44.45 mmol) and triphenylphosphine (11.66 g, 44.45 mmol) were added thereto and kept at 0° C. Diisopropyl azodicarboxylate (8.99 g, 44.45 mmol) was added dropwise to the mixture, followed by stirring for 2 hrs at room temperature. The resulting mixture washed with saturated saline and extracted with ethyl acetate. The organic layer was separated, dried over anhydrous MgSO$_4$, and concentrated under a reduced pressure. The resulting residue was purified by flash chromatography to obtain 14 g of the titled compound (yield: 93%) as a red solid.

$^1$H-NMR (200 MHz, CDCl$_3$) δ 7.45 (s, 5H), 7.18 (d, J=2 Hz, 1H), 7.07 (d, J=7.8 Hz, 1H), 6.84 (m, 1H), 4.14~4.12 (m, 4H), 2.80 (t, J=5.6 Hz, 2H), 2.78~2.57 (m, 4H), 1.14 (t, J=7.1 Hz, 3H)

Step 2) Preparation of 1-hydroxy-6-(2-morpholine-4-yl-ethoxy)-1,3-diphenyl-1H-indene-2-carboxylic Acid Ethyl Ester 6-(2-Morpholine-4-ylethoxy)-1-oxo-3-phenyl-1H-indene-2-carboxylic acid ethyl ester (1.5 g, 3.68 mmol) obtained in Step 1 was dissolved in THF, and phenylmagnesium chloride (3.865 mL, 5.89 mmol) was added thereto, followed by stirring for 2 hrs at 0° C. The resulting mixture washed with saturated saline and extracted with ethyl acetate. The organic layer was separated, dried over anhydrous MgSO$_4$, and concentrated under a reduced pressure. The resulting residue was purified by flash chromatography to obtain 788 mg of the titled compound (yield: 44%).

Example 9

Preparation of 1-hydroxy-6-morpholine-4-ylmethyl-1,3-diphenyl-1H-indene-2-carboxylic Acid Ethyl Ester Step 1) Preparation of 3-oxo-3-m-tolylpropionic Acid-ethyl Ester Sodium hydride (3.1 g, 77.1 mmol) and diethylcarbonate were added to 3-methyl acetophenone (40.5 g, 33.54 mmol). The reaction mixture was stirred for 2 hrs with heating at 80° C. Once the reaction was completed, ice water and acetic acid were added thereto. The resulting mixture washed with saturated saline and extracted with ethyl acetate. The organic layer was separated, dried over anhydrous MgSO$_4$ and concentrated under a reduced pressure. The resulting residue was purified by flash chromatography to obtain 5.8 g of the titled compound (yield: 84%).

$^1$H-NMR (200 MHz, CDCl$_3$) δ 7.83~7.63 (m, 2H) 7.42~7.28 (m, 2H) 4.27~4.18 (m, 2H) 3.97 (s, 2H) 2.40 (s, 3H) 1.36~1.23 (m, 3H)

Step 2) Preparation of 2-(3-methylbenzoyl)-3-phenyl Acrylic Acid Ethyl Ester

3-Oxo-3-m-tolylpropionic acid-ethyl ester (1 g, 4.84 mmol) obtained in Step 1 was dissolved in benzene, and benzaldehyde, acetic acid (0.15 g, 2.49 mmol) and piperidine (0.06 g, 0.8 mmol) were added thereto, followed by refluxing for 4 hrs. Upon the completion of the reaction, the mixture washed successively with saturated saline and saturated sodium bicarbonate, and extracted with ethyl acetate. The organic layer was separated, dried over anhydrous MgSO$_4$ and concentrated under a reduced pressure. The resulting residue was purified by flash chromatography to obtain 1 g of the titled compound (yield: 70%).

¹H-NMR (200 MHz, CDCl₃) δ 7.98 (s, 1H) 7.86~7.73 (m, 2H) 7.35~7.21 (m, 7H) 4.26~4.19 (m, 2H) 2.39 (s, 3H) 1.20~1.16 (m, 3H)

Step 3) Preparation of 5-methyl-3-oxo-1-phenylindene-2-carboxylic Acid Ethyl Ester 2-(3-Methylbenzoyl)-3-phenyl acrylic acid ethyl ester (1 g, 3.39 mmol) obtained in Step 2 was dissolved in dichloromethane, and methanesulfonic acid (5.22 g, 54.35 mmol) was added thereto, followed by stirring for 3 hrs at RT. Once the reaction was completed, the mixture was cooled to 0° C., neutralized with sodium bicarbonate, and extracted with dichloromethane. The organic layer was separated, dried over anhydrous MgSO₄ and concentrated under a reduced pressure. The resulting residue was purified by flash chromatography to obtain 273 mg of the titled compound (yield: 27%).

¹H-NMR (200 MHz, CDCl₃) δ 7.73~7.61 (m, 1H) 7.48~7.04 (m, 7H) 4.98~4.94 (m, 1H) 4.29~4.22 (m, 2H) 3.67~3.60 (m, 1H) 2.41 (s, 3H) 1.33~1.13 (m, 3H)

Step 4) Preparation of 6-methyl-1-oxo-3-phenyl-1H-indene-2-carboxylic Acid Ethyl Ester Phenylselenyl chloride (72 mg, 0.37 mmol) was dissolved in dichloromethane and cooled to 0° C., and pyridine (32 mg, 1.2 mmol) was added thereto. The mixture was stirred for about 20 minutes. To the mixture, 5-methyl-3-oxo-1-phenyl-indene-2-carboxyl acid ethyl ester (100 mg, 0.34 mmol) obtained in Step 3 dissolved in methane was added, followed by stirring for 2 hrs at RT. Once the reaction was completed, 10% hydrochloric acid (5 mL) was added thereto and cooled to 0° C., and 30% peroxide (1 mL) and water (5 mL) were added thereto. The resulting mixture was extracted with dichloromethane. The organic layer was separated, dried over anhydrous MgSO₄ and concentrated under a reduced pressure. The resulting residue was purified by flash chromatography to obtain 51 mg of the titled compound (yield: 51%).

¹H-NMR (200 MHz, CDCl₃) δ 7.51~7.04 (m, 8H) 4.24~4.12 (m, 2H) 2.39 (s, 3H) 1.25~1.12 (m, 3H)

Step 5) Preparation of 6-bromomethyl-1-oxo-3-phenyl-1H-indene-2-carboxylic Acid Ethyl Ester 6-Methyl-1-oxo-3-phenyl-1H-indene-2-carboxylic acid ethyl ester (3 g, 10.3 mmol) obtained in Step 4 was dissolved in carbon tetrachloride, and N-bromosuccinimide (2 g, 11.4 mmol) and 2,2'-azobisisobutyronitrile (500 mg, 3.09 mmol) were added thereto. The mixture was refluxed for 3 hrs under the irradiation of a 375 W tungsten lamp. Upon the completion of the reaction, the resulting mixture washed with saturated saline and extracted with dichloromethane. The organic layer was separated, dried over anhydrous MgSO₄ and concentrated under a reduced pressure. The resulting residue was purified by flash chromatography to obtain 1.4 g of the titled compound (yield: 36.7%) in oil state.

¹H-NMR (200 MHz, CDCl₃) δ 7.79~7.16 (m, 8H), 4.50 (s, 2H), 4.26 (q, J=7.1 Hz, 2H), 1.16 (t, J=7.1 Hz, 3H)

Step 6) Preparation of 6-morpholine-4-ylmethyl-1-oxo-3-phenyl-1H-indene-2-carboxylic Acid Ethyl Ester 6-Bromomethyl-1-oxo-3-phenyl-1H-indene-2-carboxylic acid ethyl ester (1.1 g, 2.96 mmol) obtained in Step 5 was dissolved in N,N-dimethyl formamide. Pyridine (264 μl, 3.26 mmol) and morpholine (284 μl, 3.26 mmol) were added thereto, followed by stirring for 2 hrs. Upon the completion of the reaction, the resulting mixture washed successively with saturated ammonium chloride and saline and extracted with ethyl acetate. The organic layer was separated, dried over anhydrous MgSO₄ and concentrated under a reduced pressure. The resulting residue was purified by flash chromatography to obtain 180 mg of the titled compound (yield: 16.1%) in red oil state.

¹H-NMR (200 MHz, CDCl₃) δ 7.61~7.11 (m, 8H), 4.19 (q, J=7.1 Hz, 2H), 3.70 (t, J=4.8 Hz, 4H), 3.51 (s, 2H), 2.44 (t, J=4.8 Hz, 4H), 1.15 (t, J=7.1 Hz, 3H)

Step 7) Preparation of 1-hydroxy-6-morpholine-4-ylmethyl-1,3-diphenyl-1H-indene-2-carboxylic Acid Ethyl Ester 6-Morpholine-4-yl-methyl-1-oxo-3-phenyl-1H-indene-2-carboxylic acid ethyl ester (30 mg, 0.08 mmol) obtained in Step 6 was dissolved in THF, and phenylmagnesium chloride (0.12 mL, 0.24 mmol) was added thereto, followed by stirring for 2 hrs at 0° C. Upon the completion of the reaction, the mixture was washed with saturated saline and extracted with ethyl acetate. The organic layer was separated, dried over anhydrous MgSO₄ and concentrated under a reduced pressure. The resulting residue was purified by flash chromatography to obtain 10 mg of the titled compound (yield: 27%).

Example 10

Preparation of 1-hydroxy-1,3-diphenyl-6-(2-pyridine-2-yl-ethoxy)-1H-indene-2-carboxylic Acid Ethyl Ester 6-Hydroxy-1-oxo-3-phenyl-1H-indene-2-carboxylic acid ethyl ester (300 mg, 1.019 mmol) obtained in Preparation Example 2 was dissolved in THF/benzene (30 mL/10 mL). 2-Pyridine ethanol (308 mg, 2.039 mmol) and triphenyl phosphine (534 mg, 2.039 mmol) were added thereto, and cooled to 0° C. Subsequently, diisopropyl azodicarboxylate (412 mg, 2.039 mmol) was slowly dropped thereto and stirred for 1 hr at RT. The resulting mixture washed with saturated saline and extracted with ethyl acetate. The organic layer was separated, dried over anhydrous MgSO₄ and concentrated under a reduced pressure. The resulting residue was purified by flash chromatography to obtain 388 g of 6-[2-(pyridine-2-yl)-ethoxy]-1-oxo-3-phenyl-1H-indene-2-carboxylic acid ethyl ester (yield: 89%) as a red solid.

Then, 1-oxo-3-phenyl-6-(2-pyridine-2-yl-ethoxy)-1H-indene-2-carboxylic acid ethyl ester (60 mg, 0.15 mmol) thus obtained was dissolved in THF and phenylmagnesium chloride (0.15 mL, 0.3 mmol) was added thereto. The mixture was stirred for 5 minutes at RT, washed with sodium chloride solution and extracted with ethyl acetate. The organic layer was separated, dried over anhydrous MgSO₄ and concentrated under a reduced pressure. The resulting residue was purified by flash chromatography to obtain 44 mg of the titled compound (yield: 61%)

Example 11

Preparation of 1-hydroxy-1,3-diphenyl-6-(3-phenyl-propoxy)-1H-indene-2-carboxylic Acid Ethyl Ester Step 1) Preparation of 3-phenyl-6-(3-phenyl-propoxy)-indene-1-one 3-Phenyl-1-[3-(3-phenyl-propoxy)-phenyl]-propenone (20 g, 58.406 mmol) and polyphosphoric acid (200 g) were mixed and stirred for 6 hrs at 45° C. The reaction mixture washed with water and extracted with ethyl acetate. The organic layer was separated, dried over anhydrous MgSO$_4$ and concentrated under a reduced pressure. The resulting residue was purified by flash chromatography (ethyl acetate: hexane=1:5) to obtain 17.9 g of the titled compound (yield: 81%) as a white solid.

$^1$H-NMR (200 MHz, CDCl$_3$) δ 7.36~7.09 (m, 13H), 4.52 (dd, J=7.8, 3.6 Hz, 1H), 4.01 (t, J=6.3 Hz, 2H), 3.25 (dd, J=19.3, 7.7 Hz, 1H), 2.81 (t, J=7.1 Hz, 2H), 2.68 (dd, J=19.3, 3.6 Hz, 1H), 2.14 (m, 2H)

Step 2) Preparation of 2-bromo-3-phenyl-6-(3-phenyl-propoxy)-indene-1-one

3-Phenyl-6-(3-phenyl-propoxy)-indene-1-one (200 mg, 0.586 mmol) obtained in Step 1 was dissolved in carbon tetrachloride, and N-bromosuccinimide (313 mg, 1.75 mmol) and 2,2'-azobisisobutyronitrile (9.7 mg) were added thereto. The mixture was refluxed for 1 hr under the irradiation of a 375 W tungsten lamp. Upon the completion of the reaction, the mixture washed with saturated saline and extracted with dichloromethane. The organic layer was separated, dried over anhydrous MgSO$_4$ and concentrated under a reduced pressure. The resulting residue was purified by flash chromatography (ethyl acetate:hexane=1:5) to obtain 147 mg of the titled compound (yield: 60%) as a red solid.

$^1$H-NMR (200 MHz, CDCl$_3$) δ 7.69~7.16 (m, 11H), 7.02 (d, J=8.2 Hz, 1H), 6.74 (dd, J=8.2, 2.3 Hz, 1H), 3.97 (t, J=6.4 Hz, 2H), 2.81 (t, J=6.3 Hz, 2H), 2.11 (m, 2H)

Step 3) Preparation of 1-oxo-3-phenyl-6-(3-phenyl-propoxy)-1H-indene-2-carbonitrile 2-Bromo-3-phenyl-6-(3-phenyl-propoxy)-indene-1-one (1.0 g, 2.3 mmol) obtained in Step 2 was dissolved in N,N-dimethyl formamide (10 mL), copper(I) cyamide (617 mg, 6.9 mmol) was added thereto, and the mixture was stirred for 3 hrs at 150° C., followed by cooling. The resulting mixture was washed with saturated ammonium chloride and extracted with ethyl acetate. The organic layer was separated, dried over anhydrous MgSO$_4$ and concentrated under a reduced pressure. The resulting residue was purified by flash chromatography (ethyl acetate:hexane=1:3) to obtain 700 mg of the titled compound (yield: 80%) as a red solid.

$^1$H-NMR (200 MHz, CDCl$_3$) δ 7.83~7.18 (m, 12H), 6.89 (dd, J=8.2, J=2.3 Hz, 1H), 4.02 (t, J=6.5 Hz, 2H), 2.81 (t, J=6.3 Hz, 2H), 2.13 (m, 2H)

Step 4) Preparation of 1-hydroxy-1,3-diphenyl-6-(3-phenylpropoxy)-1H-indene-2-carboxylic Acid Ethyl Ester 1-Oxo-3-phenyl-6-(3-phenyl-propoxy)-1H-indene-2-carbonitrile (100 mg, 0.274 mmol) obtained in Step 3 was dissolved in THF under a N$_2$ gas atmosphere, and phenylmagnesium chloride (2M sol, 0.131 μL) was added thereto, followed by stirring for 2 hrs at 0° C. The resulting mixture washed with saturated ammonium chloride and extracted with ethyl acetate. The organic layer was separated, dried over anhydrous MgSO$_4$ and concentrated under a reduced pressure. Then, the resulting residue was purified by flash chromatography to obtain 80.7 mg of the titled compound (yield: 66%) as a pink solid.

$^1$H-MR (200 MHz, CDCl$_3$) δ 7.70~6.90 (m, 18H), 3.95 (t, J=6.2 Hz, 2H), 2.77 (t, J=7.4 Hz, 2H), 2.10~2.04 (m, 2H)

Example 12

Preparation of 1-hydroxy-1,3-diphenyl-6-(3-phenyl-propoxy)-1H-indene-2-carboxylic Acid Methyl Ester Step 1) Preparation of 1-oxo-3-phenyl-6-(3-phenyl-propoxy)-1H-indene-2-carboxylic Acid Methyl Ester 1-Oxo-3-phenyl-6-(3-phenylpropoxy)-1H-indene-2-carboxylic acid ethyl ester (2 g, 4.85 mmol) obtained in Example 7 was dissolved in methanol, p-toluenesulfonic acid (92 mg, 0.49 mmol) was added thereto, and refluxed for 24 hrs. The resulting mixture washed with sodium bicarbonate and extracted with ethyl acetate. The organic layer was separated, dried over anhydrous MgSO$_4$ and concentrated under a reduced pressure. Then, the resulting residue was purified by flash chromatography to obtain 1.2 g of the titled compound (yield: 62%).

$^1$H-NMR (200 MHz, CDCl$_3$) δ 7.51~6.78 (m, 13H), 4.01 (t, J=6.0 Hz, 2H), 3.72 (s, 3H), 2.81 (t, J=7.2, 2H), 2.11 (m, 2H)

Step 2) Preparation of 1-hydroxy-1,3-diphenyl-6-(3-phenyl-propoxy)-1H-indene-2-carboxylic Acid Methyl Ester 1-Oxo-3-phenyl-6-(3-phenylpropoxy)-1H-indene-2-carbonitrile (350 mg, 0.878 mmol) obtained in Step 1 was dissolved in THF, and phenylmagnesium chloride (0.483 mL, 0.966 mmol) was added thereto, followed by stirring for 3 hrs at 0° C. Upon the completion of the reaction, the mixture washed with saturated saline and extracted with ethyl acetate. The organic layer was separated, dried over anhydrous MgSO$_4$ and concentrated under a reduced pressure. The resulting residue was purified by flash chromatography to obtain 378 mg of the titled compound (yield: 90%).

Example 13

Preparation of 1-hydroxy-6-methoxy-1,3-diphenyl-1H-indene-2-carboxylic Acid

1-Hydroxy-6-methoxy-1,3-diphenyl-1H-indene-2-carboxylic acid ethyl ester (110 mg, 0.285 mmol) prepared in Example 1 was dissolved in THF, and an excess amount of sodium hydroxide dissolved in aqueous ethanol was added thereto in such a way not to cause layer separation. The mixture was stirred for 24 hrs at RT, and the pH was adjusted to 3~4 using 2N hydrochloric acid. The resulting mixture was extracted with ethyl acetate. The organic layer was separated, dried over anhydrous MgSO$_4$ and concentrated under a reduced pressure, to obtain 99 mg of the titled compound (yield: 97%).

Example 14

Preparation of 1-hydroxy-6-methoxy-1-methyl-3-phenyl-1H-indene-2-carboxylic Acid 1-Hydroxy-6-methoxy-1-methyl-3-phenyl-1H-indene-2-carboxylic acid ethyl ester (100 mg, 0.309 mmol) prepared in Example 4 was dissolved in THF, and an excess amount of sodium hydroxide dissolved in aqueous ethanol was added thereto in such a way not to cause layer separation. The mixture was stirred for 24 hrs at RT, and the pH was adjusted to 3~4 using 2N hydrochloric acid. The resulting mixture was extracted with ethyl acetate. The organic layer was separated, dried over anhydrous MgSO₄ and concentrated under a reduced pressure, to obtain 63 mg of the titled compound (yield: 69%).

Example 15

Preparation of 1-benzyl-1-hydroxy-6-methoxy-3-phenyl-1H-indene-2-carboxylic Acid 1-Benzyl-1-hydroxy-6-methoxy-3-phenyl-1H-indene-2-carboxylic acid ethyl ester (35 mg, 0.087 mmol) prepared in Example 5 was dissolved in THF, and an excess amount of sodium hydroxide dissolved in aqueous ethanol was added thereto in such a way not to cause layer separation. The mixture was stirred for 24 hrs at RT, and the pH was adjusted to 3~4 using 2N hydrochloric acid. The resulting mixture was extracted with ethyl acetate. The organic layer was separated, dried over anhydrous MgSO₄ and concentrated under a reduced pressure, to obtain 35 mg of the titled compound (yield: 100%).

Example 16

Preparation of 1-hydroxy-1,3-diphenyl-6-(3-phenyl-propoxy)-1H-indene-2-carboxylic Acid 1-Hydroxy-1,3-diphenyl-6-(3-phenyl-propoxy)-1H-indene-2-carboxylic acid ethyl ester (200 mg, 0.408 mmol) prepared in Example 7 was dissolved in THF, and an excess amount of sodium hydroxide dissolved in aqueous ethanol was added thereto in such a way not to cause layer separation. The mixture was stirred for 5 hrs at RT, and the pH was adjusted to 3~4 using 2N hydrochloric acid. The resulting mixture was extracted with ethyl acetate. The organic layer was separated, dried over anhydrous MgSO₄ and concentrated under a reduced pressure, to obtain 85 mg of the titled compound (yield: 45%).

Example 17

Preparation of 1-cyclohexyl-1-hydroxy-6-methoxy-3-phenyl-1H-indene-2-carboxylic Acid 1-Cyclohexyl-1-hydroxy-6-methoxy-3-phenyl-1H-indene-2-carboxylic acid ethyl ester (20 mg, 0.051 mmol) prepared in Example 6 was dissolved in THF, and an excess amount of sodium hydroxide dissolved in aqueous ethanol was added thereto in such a way not to cause layer separation. The mixture was stirred for 24 hrs at RT, and the pH was adjusted to 3~4 using 2N hydrochloric acid. The resulting mixture was extracted with ethyl acetate. The organic layer was separated, dried over anhydrous MgSO₄ and concentrated under a reduced pressure, to obtain 15 mg of the titled compound (yield: 80%).

Example 18

Preparation of 1,6-dimethoxy-3-phenyl-1H-indene-2-carboxylic Acid Ethyl Ester

Step 1) Preparation of 1-bromo-6-methoxy-3-phenyl-1H-indene-2-carboxylic Acid Ethyl Ester 6-Methoxy-3-phenyl-1H-indene-2-carboxylic acid ethyl ester (1.5 g, 5.10 mmol) prepared in Preparation Example 1 was dissolved in dichloromethane (80 mL), and N-bromosuccinimide (1.09 g, 6.12 mmol) and 2,2'-azobisisobutyronitrile (0.08 mg, 0.51 mmol) were added thereto. The mixture was stirred for 2 hrs at RT under the irradiation of a 375 W tungsten lamp. Upon the completion of the reaction, the mixture washed with saturated saline and extracted with dichloromethane. The organic layer was separated, dried over anhydrous MgSO₄ and concentrated under a reduced pressure. The resulting residue was purified by flash chromatography (ethyl acetate/n-hexane=1/20→1/9) to obtain 1.4 g of the titled compound (yield: 74%) as a yellow solid.

$^1$H-NMR (300 MHz, CDCl₃) δ 7.46-7.42 (m, 5H) 7.21 (d, J=2.4 Hz, 1H) 7.13 (d, J=8.4 Hz, 1H) 6.86 (dd, J=8.4, 2.4 Hz, 1H) 5.85 (s, 1H) 4.25-4.10 (m, 2H) 3.88 (s, 3H) 1.15 (t, J=7.2 Hz, 3H)

Step 2) Preparation of 1,6-dimethoxy-3-phenyl-1H-indene-2-carboxylic Acid Ethyl Ester 1-Bromo-6-methoxy-3-phenyl-1H-indene-2-carboxylic acid ethyl ester (60 mg, 0.18 mmol) obtained in Step 1 was dissolved in methanol (10 mL), silver nitrate (37.20 mg, 0.22 mmol) was added thereto, stirred for 3 hrs at RT, and filtered. The organic layer was separated, and concentrated under a reduced pressure. The resulting residue was purified by flash chromatography to obtain 14 mg of the titled compound (yield: 24%).

Example 19

Preparation of 1-ethoxy-6-methoxy-3-phenyl-1H-indene-2-carboxylic Acid Ethyl Ester 1-Bromo-6-methoxy-3-phenyl-1H-indene-2-carboxylic acid ethyl ester (30 mg, 0.09 mmol) obtained in Example 18 was dissolved in ethanol (3 mL), silver nitrate (15.50 mg, 0.09 mmol) was added thereto, stirred for 3.5 hrs at RT, and filtered. The organic layer was separated, and concentrated under a reduced pressure. The resulting residue was purified by flash chromatography to obtain 16 mg of the titled compound (yield: 52%).

Example 20

Preparation of 1-amino-6-methoxy-3-phenyl-1H-indene-2-carboxylic Acid Ethyl Ester Step 1) Preparation of 1-hydroxyimino-6-methoxy-3-phenyl-1H-indene-2-carboxylic Acid Ethyl Ester 6-Methoxy-1-oxo-3-phenyl-1H-indene-2-carboxylic acid ethyl ester (1.6 g, 5.19 mmol) obtained in Example 1 was dissolved in ethanol (100 mL), hydroxylamine hydrochloride (1.08 g, 15.57 mmol) and pyridine (1.64 g, 1.68 mL, 20.76 mmol) were added thereto, refluxed for 1 hr, and cooled to RT. The resulting mixture washed with saturated sodium bicarbonate and extracted with ethyl acetate. The organic layer was separated, dried over anhydrous MgSO₄ and concentrated under a reduced pressure. The resulting residue was purified by flash chromatography to obtain 1.34 g of the titled compound (yield: 80%).

$^1$H-NMR (300 MHz, CDCl₃) δ 11.41 (brs, 1H) 8.10 (d, J=2.4 Hz, 1H) 7.47-7.42 (m, 5H) 7.12 (d, J=8.4 Hz, 1H) 6.88 (dd, J=8.4, 2.4 Hz, 1H) 4.17 (q, J=14.4, 7.2 Hz, 2H) 3.89 (s, 3H) 1.06 (t, J=7.2 Hz, 3H)

Step 2) Preparation of 1-amino-6-methoxy-3-phenyl-1H-indene-2-carboxylic Acid Ethyl Ester 1-Hydroxyimino-6-methoxy-3-phenyl-1H-indene-2-carboxylic acid ethyl ester (1.00 g, 3.09 mmol) obtained in Step 1 was dissolved in methanol (100 mL), and 10%-palladium (583 mg) was added thereto. The mixture was stirred for 15 hrs at RT while providing $H_2$ gas thereto using a balloon, filtered through celite, and concentrated under a reduced pressure. The resulting residue was purified by flash chromatography to obtain 786 mg of the titled compound (yield: 82%).

Example 21

Preparation of 1-amino-3-phenyl-6-(3-phenyl-propoxy)-1H-indene-2-carboxylic Acid Ethyl Ester

Step 1) Preparation of 1-hydroxyimino-3-phenyl-6-(3-phenylpropoxy)-1H-indene-2-carboxylic Acid Ethyl Ester 1-Oxo-3-phenyl-6-(3-phenyl-propoxy)-1H-indene-2-carboxylic acid ethyl ester (1.5 g, 3.64 mmol) obtained in Example 7 was dissolved in ethanol (100 mL), hydroxylamine hydrochloride (759 mg, 10.92 mmol) and pyridine (1.15 g, 15.56 mmol) were added thereto, refluxed for 1 hr, and cooled to RT. The resulting mixture washed with saturated sodium bicarbonate and extracted with ethyl acetate. The organic layer was separated, dried over anhydrous $MgSO_4$ and concentrated under a reduced pressure. The resulting residue was purified by flash chromatography to obtain 0.91 g of the titled compound (yield: 58%).

$^1$H-NMR (300 MHz, $CDCl_3$) δ 11.3 (brs, 1H) 8.10 (d, J=2.4 Hz, 1H) 7.47-7.42 (m, 10H) 7.12 (d, J=8.4 Hz, 1H) 6.88 (dd, J=8.4, 2.4 Hz, 1H) 4.17 (q, J=7.2 Hz, 2H) 4.04 (t, J=6.8 Hz, 2H) 2.83 (t, J=6.8 Hz, 2H) 2.11 (quint, J=6.8 Hz, 2H) 1.06 (t, J=7.2 Hz, 3H)

Step 2) Preparation of 1-amino-3-phenyl-6-(3-phenyl-propoxy)-1H-indene-2-carboxylic Acid Ethyl Ester 1-Hydroxyimino-3-phenyl-6-(3-phenylpropoxy)-1H-indene-2-carboxylic acid ethyl ester (0.5 g, 1.17 mmol) obtained in Step 1 was dissolved in methanol (30 mL) and 10%-palladium (400 mg) was added thereto. The mixture was stirred for 15 hrs at RT while providing $H_2$ gas thereto using a balloon, filtered through celite, and concentrated under a reduced pressure. The resulting residue was purified by flash chromatography to obtain 377 mg of the titled compound (yield: 78%).

Example 22

Preparation of 1-amino-6-(2-morpholine-4-yl-ethoxy)-3-phenyl-1H-indene-2-carboxylic Acid Cyclohexylamide

Step 1) Preparation of 6-hydroxy-1-oxo-3-phenyl-1H-indene-2-carboxylic Acid Methyl Ester 6-Hydroxy-1-oxo-3-phenyl-1H-indene-2-carboxylic acid ethyl ester (500 mg, 1.70 mmol) prepared in Preparation Example 2 was dissolved in methanol (30 mL), p-toluenesulfonic acid (65 mg, 0.34 mmol) was added thereto, refluxed for 24 hrs, and the solvent was removed therefrom by evaporation. The resulting residue was purified by flash chromatography to obtain 470 mg of the titled compound (yield: 98.6%) as a red solid.

$^1$H-NMR (300 MHz, $CDCl_3$) δ 7.75~6.81 (m, 8H), 3.73 (s, 3H)

Step 2) Preparation of 6-hydroxy-1-oxo-3-phenyl-1H-indene-2-carboxylic Acid

6-Hydroxy-1-oxo-3-phenyl-1H-indene-2-carboxylic acid methyl ester (2.6 g, 9.28 mmol) obtained in Step 1 was dissolved in dichloroethane, and boron tribromide methyl sulfide (6.0 mL, 27.84 mmol) was added thereto. The mixture was refluxed for 2 hrs at 90° C., cooled in an ice bath, neutralized using sodium bicarbonate, and adjusted to pH 2 using 6N hydrochloric acid. The resulting mixture washed successively with dichloromethane and water. The organic layer was separated, dried over anhydrous $MgSO_4$, concentrated under a reduced pressure and recrystallized to obtain 1.2 g of the titled compound (yield: 48.6%).

$^1$H-NMR (300 MHz, $CDCl_3$) δ 7.79~6.84 (m, 8H)

Step 3) Preparation of 6-hydroxy-1-oxo-3-phenyl-1H-indene-2-carboxylic Acid Cyclohexylamide 6-Hydroxy-1-oxo-3-phenyl-1H-indene-2-carboxylic acid (100 mg, 0.38 mmol) obtained in Step 2 was dissolved in dichloromethane, and triethylamine (175 μl, 1.25 mmol) and cyclohexylamine (43 μl, 0.38 mmol) were added thereto at 10° C. Then, bis(2-oxo-3-oxazoline)phosphoryl chloride (100 mg, 0.38 mmol) was further added thereto, stirred for 10~20 minutes at RT, and then stirred for additional 1 hr in a water bath. After water was added to complete the reaction, the mixture washed with sodium bicarbonate and extracted with dichloromethane. The organic layer was separated, dried over anhydrous $MgSO_4$, concentrated under a reduced pressure. The resulting residue was purified by flash chromatography to obtain 26 mg of the titled compound (yield: 20.0%) as a red solid.

$^1$H-NMR (300 MHz, $CDCl_3$) δ 7.68~6.80 (m, 8H), 3.87 (m, 1H), 1.80~1.34 (m, 10H)

Step 4) Preparation of 6-(2-morpholine-4-ylethoxy)-1-oxo-3-phenyl-1H-indene-2-carboxylic Acid Cyclohexylamide 6-Hydroxy-1-oxo-3-phenyl-1H-indene-2-carboxylic acid cyclohexylamide (141 mg, 0.41 mmol) obtained in Step 3 was dissolved in tetrahydropyran/benzene (3 mL/2 mL), and 4-(2-hydroxyethyl)morpholine (99 μl, 0.82 mmol) and triphenylphosphine (215 mg, 0.82 mmol) were added thereto. Then, diisopropyl azodicarboxylate (149 μl, 0.82 mmol) was added slowly thereto at 0° C., and stirred for 2 hrs at RT. The resulting mixture washed with saturated saline and extracted with ethyl acetate. The organic layer was separated, dried over anhydrous $MgSO_4$ and concentrated under a reduced pressure. The resulting residue was purified by flash chromatography to obtain 165 mg of the titled compound (yield: 88.3%).

$^1$H-NMR (200 MHz, $CDCl_3$) δ 7.92~6.85 (m, 8H), 4.16 (t, J=5.4 Hz, 2H), 3.86 (m, 1H), 3.73 (t, J=4.8 Hz, 4H), 2.82 (t, J=5.4 Hz, 2H) 2.57 (t, J=4.8 Hz, 4H), 1.81~1.34 (m, 10H)

Step 5) Preparation of 1-amino-6-(2-morpholine-4-yl-ethoxy)-3-phenyl-1H-indene-2-carboxylic Acid Cyclohexylamide 6-(2-Morpholine-4-ylethoxy)-1-oxo-3-phenyl-1H-indene-2-carboxylic acid cyclohexylamide (130 mg, 0.28%) obtained in Step 4 was dissolved in ethanol (20 mL), and hydroxylamine hydrochloride (60 mg, 0.85 mmol) and pyridine (892 mg, 1.13 mmol) were added thereto. The mixture was refluxed for 1 hr, and cooled to RT, and extracted with dichloromethane. The organic layer was separated, dried over anhydrous $MgSO_4$ and concentrated under a reduced pressure. The resulting residue was purified by flash chromatography to obtain 86 mg of 1-hydroxyimino-6-(2-morpholine-4-yl-ethoxy)-3-phenyl-1H-indene-2-carboxylic acid cyclohexylamide (yield: 64%). Subsequently, 1-hydroxyimino-6-(2-morpholine-4-yl-ethoxy)-3-phenyl-1H-indene-2-carboxylic acid cyclohexylamide (80 mg, 0.17 mmol) thus obtained was dissolved in methanol (20 mL) and 10%-palladium (100 mg) was added thereto. The mixture was stirred for 15 hrs at RT while providing $H_2$ gas thereto using a balloon, filtered through celite, and concentrated under a reduced pressure. Then, the resulting residue was purified by flash chromatography to obtain 14 mg of the titled compound (yield: 18%).

Example 23

Preparation of 1-amino-3-phenyl-6-(3-phenyl-propoxy)-1H-indene-2-carbonitrile

1-Oxo-3-phenyl-6-(3-phenyl-propoxy)-1H-indene-2-carbonitrile (293 mg, 0.80 mmol) obtained in Example 11 was dissolved in ethanol (20 mL), and hydroxylamine hydrochloride (167 mg, 2.41 mmol) and pyridine (254 mg, 3.21 mmol) were added thereto, refluxed for 3 hrs, and cooled to RT. The resulting mixture washed with saturated sodium bicarbonate, extracted with ethyl acetate. The organic layer was separated, dried over anhydrous $MgSO_4$ and concentrated under a reduced pressure. The resulting residue was purified by flash chromatography to obtain 230 mg of 1-hydroxyimino-3-phenyl-6-(3-phenyl-propoxy)-1H-indene-2-carbonitrile (yield: 75%). Subsequently, 1-hydroxyimino-3-phenyl-6-(3-phenyl-propoxy)-1H-indene-2-carbonitrile (230 mg, 0.60 mmol) thus obtained was dissolved in methanol (20 mL), and 10%-palladium (230 mg) was added thereto. The mixture was stirred for 15 hrs at RT while providing $H_2$ gas thereto using a balloon, filtered through celite, and concentrated under a reduced pressure. The resulting residue was purified by flash chromatography to obtain 90 mg of the titled compound (yield: 41%).

Example 24

Preparation of 1-acetylamino-6-methoxy-3-phenyl-1H-indene-2-carboxylic Acid Ethyl Ester 1-Amino-6-methoxy-3-phenyl-1H-indene-2-carboxylic acid ethyl ester (60 mg, 0.19 mmol) prepared in Example 20 was dissolved in dichloromethane (10 mL), and acetyl chloride (76.15 mg, 70.0 μl, 0.97 mmol) and triethylamine (130.00 mg, 0.18 mL, 128 mmol) were added thereto in order at 0° C. The mixture was stirred for 1 hr at RT, washed with saturated saline and extracted with dichloromethane. The organic layer was separated, dried over anhydrous $MgSO_4$ and concentrated under a reduced pressure. The resulting residue was purified by flash chromatography to obtain 48 mg of the titled compound (yield: 71%).

Example 25

Preparation of 6-methoxy-3-phenyl-1-propionylamino-1H-indene-2-carboxylic Acid Ethyl Ester 1-Amino-6-methoxy-3-phenyl-1H-indene-2-carboxylic acid ethyl ester (50 mg, 0.16 mmol) prepared in Example 20 was dissolved in dichloromethane (10 mL), and propionyl chloride (150.38 mg, 0.14 mL, 1.62 mmol) and triethylamine (180.12 mg, 0.25 mL, 1.78 mmol) were added thereto in order at 0° C. The mixture was stirred for 24 hrs at RT, and an excess amount of propionyl chloride (2 mL) was further added thereto to be stirred for 15 hrs. The resulting mixture was washed with saturated saline and extracted with dichloromethane. The organic layer was separated, dried over anhydrous $MgSO_4$ and concentrated under a reduced pressure. The resulting residue was purified by flash chromatography to obtain 29 mg of the titled compound (yield: 50%).

Example 26

Preparation of 1-acetylamino-3-phenyl-6-(3-phenyl-propoxy)-1H-indene-2-carboxylic Acid Ethyl Ester 1-Amino-3-phenyl-6-(3-phenyl-propoxy)-1H-indene-2-carboxylic acid ethyl ester (30 mg, 0.07 mmol) prepared in Example 21 was dissolved in dichloromethane (10 mL), and acetyl chloride (30.15 mg, 0.37 mmol) and triethylamine (40 mg, 0.37 mmol) were added thereto in order at 0° C. The mixture was stirred for 24 hrs at RT, washed with saturated saline and extracted with dichloromethane. The organic layer was separated, dried over anhydrous $MgSO_4$ and concentrated under a reduced pressure. The resulting residue was purified by flash chromatography to obtain 15 mg of the titled compound (yield: 45%).

Example 27

Preparation of 1-acetylamino-6-(2-morpholine-4-yl-ethoxy)-3-phenyl-1H-indene-2-carboxylic Acid Cyclohexylamide 1-Amino-6-(2-morpholine-4-yl-ethoxy)-3-phenyl-1H-indene-2-carboxylic acid cyclohexylamide (14 mg, 0.03 mmol) prepared in Example 22 was dissolved in dichloromethane (10 mL), acetyl chloride (24 mg, 0.3 mmol) and triethylamine (30 mg, 0.3 mmol) were added thereto in order at 0° C., and stirred for 24 hrs at RT. The resulting mixture washed with saturated saline and extracted with dichloromethane. The organic layer was separated, dried over anhydrous $MgSO_4$ and concentrated under a reduced pressure. The resulting residue was purified by flash chromatography to obtain 3 mg of the titled compound (yield: 20%).

Example 28

Preparation of 1-diethylamine-6-methoxy-3-phenyl-1H-indene-2-carboxylic Acid Ethyl Ester 1-Bromo-6-methoxy-3-phenyl-1H-indene-2-carboxylic acid ethyl ester (100 mg, 0.27 mmol) obtained in Example 18 was dissolved in THF (10 mL), and diethylamine (98.74 mg, 0.14 mL, 1.35 mmol) was added dropwise thereto. The mixture was stirred for 12 hrs at RT, and the solvent was removed under a reduced pressure. The resulting residue was purified by flash chromatography to obtain 65 mg of the titled compound (yield: 66.3%).

Example 29

Preparation of 1-ethylamino-6-methoxy-3-phenyl-1H-indene-2-carboxylic Acid Ethyl Ester 1-Bromo-6-methoxy-3-phenyl-1H-indene-2-carboxylic acid ethyl ester (100 mg, 0.27 mmol) obtained in Example 18 was dissolved in THF (10 mL), and 2.0 M ethylamine (0.68 mL, 1.35 mmol) in THF was added dropwise thereto. The mixture was stirred for 12 hrs at RT, and the solvent was removed under a reduced pressure. The resulting residue was purified by flash chromatography to obtain 68 mg of the titled compound (yield: 75.6%).

Example 30

Preparation of 6-methoxy-1-morpholine-4-yl-3-phenyl-1H-indene-2-carboxylic Acid Ethyl Ester 1-Bromo-6-methoxy-3-phenyl-1H-indene-2-carboxylic acid ethyl ester (10 mg, 0.40 mmol) obtained in Example 18 was dissolved in THF (15 mL), and morpholine (175.01 mg, 0.18 mL, 2.01 mmol) was added dropwise thereto. The mixture was stirred for 12 hrs at RT, and the solvent was removed under a reduced pressure. The resulting residue was purified by flash chromatography to obtain 126 mg of the titled compound (yield: 83%).

Example 31

Preparation of 1-benzylamino-6-methoxy-3-phenyl-1H-indene-2-carboxylic Acid Ethyl Ester 1-Bromo-6-methoxy-3-phenyl-1H-indene-2-carboxylic acid ethyl ester (120 mg, 0.32 mmol) obtained in Example 18 was dissolved in THF (10 mL), and benzylamine (102.87 mg, 0.11 mL, 0.93 mmol) and sodium iodide (9.60 mg, 0.06 mmol) were added thereto, followed by refluxing for 6 hrs. The resulting mixture washed with saturated saline and extracted with ethyl acetate. The organic layer was separated, dried over anhydrous MgSO$_4$ and concentrated under a reduced pressure. The resulting residue was purified by flash chromatography to obtain 56 mg of the titled compound (yield: 44%).

Example 32

Preparation of 1-cyclohexylamino-6-methoxy-3-phenyl-1H-indene-2-carboxylic Acid Ethyl Ester 1-Bromo-6-methoxy-3-phenyl-1H-indene-2-carboxylic acid ethyl ester (100 mg, 0.27 mmol) obtained in Example 18 was dissolved in THF (10 mL), and cyclohexylamine (132.86 mg, 0.15 mL, 1.34 mmol) was added dropwise thereto. The mixture was stirred for 12 hrs at RT, and the solvent was removed under a reduced pressure. The resulting residue was purified by flash chromatography to obtain 25 mg of the titled compound (yield: 24%).

FORMULATION EXAMPLE 1

Preparation of Syrup

A syrup containing hydrochloric acid salt of the compound of Example 8, 1-hydroxy-6-(2-morpholine-4-yl-ethoxy)-1,3-diphenyl-1H-indene-2-carboxylic acid ethyl ester, was prepared using the ingredients shown in Table 2 by dissolving 1-hydroxy-6-(2-morpholine-4-yl-ethoxy)-1,3-diphenyl-1H-indene-2-carboxylic acid ethyl ester hydrochloride, saccharine, and sugar in warm water, cooling, and adding other ingredients thereto to a volume of 100 mL.

TABLE 2

| Ingredients | Quantity |
| --- | --- |
| 1-Hydroxy-6-(2-morpholine-4-yl-ethoxy)-1,3-diphenyl-1H-indene-2-carboxylic acid ethyl ester hydrochloride | 2 g |
| Saccharine | 0.8 g |
| Sugar | 25.4 g |
| Glycerine | 8.0 g |
| Flavoring | 0.04 g |
| Ethanol | 4.0 g |
| Sorbic Acid | 0.4 g |
| Distilled Water | q.s. |

FORMULATION EXAMPLE 2

Preparation of Tablet

A tablet containing hydrochloric acid salt of the compound of Example 8 was prepared with the ingredients shown in Table 3 by mixing 1-hydroxy-6-(2-morpholine-4-yl-ethoxy)-1,3-diphenyl-1H-indene-2-carboxylic acid ethyl ester hydrochloride with lactose, potato starch and colloidal silica and adding a 10% gelatin solution thereto. Then the mixture was crushed, sieved through a 14 mesh and dried. Finally the remaining ingredients were added thereto and tableting was performed.

TABLE 3

| Ingredients | Quantity |
| --- | --- |
| 1-Hydroxy-6-(2-morpholine-4-yl-ethoxy)-1,3-diphenyl-1H-indene-2-carboxylic acid ethyl ester hydrochloride | 250 g |
| Lactose | 175.9 g |
| Potato Starch | 180 g |
| Colloidal Silica | 32 g |
| 10% gelatin solution | 25 g |
| Potato Starch | 160 g |
| Talc | 50 g |
| Magnesium Stearate | 5 g. |

FORMULATION EXAMPLE 3

Preparation of an Injectable Solution

1-Hydroxy-6-(2-morpholine-4-yl-ethoxy)-1,3-diphenyl-1H-indene-2-carboxylic acid ethyl ester hydrochloride, sodium chloride and ascorbic acid were dissolved in distilled water in amounts as shown in Table 4 and sterilized.

TABLE 4

| Ingredients | Quantity |
| --- | --- |
| 1-Hydroxy-6-(2-morpholine-4-yl-ethoxy)-1,3-diphenyl-1H-indene-2-carboxylic acid ethyl ester hydrochloride | 1 g |
| Sodium chloride | 0.6 g |
| Ascorbic acid | 0.1 g |
| Distilled water | q.s. |

TEST EXAMPLE 1

PPARγ Activation Test

The activity for PPARγ activation was examined as follows.

The vector fused with ligand binding domain of a human PPARγ gene and DNA binding site of a yeast GAL-4 gene, and luciferase reporter vector were simultaneously transfected in NIH/3T3 cell. The cells were cultured for 24 hrs. The solution containing the cells at a concentration of $2\times10^4$ cells/well was placed on a 96-well plate. Then, each of the test compounds of the present invention and the control group without test compounds was added thereto. After incubating for 24 hrs, the cells were subjected to lysis. The luciferase activity of the resultant was then measured, and the activation activity of the test compound was expressed as $EC_{50}$ (the concentration at which 50% of the maximum activation was observed) to compute the activation intensities of the test compounds and the comparative compound, rosiglitazone, relative to PPARγ. The results are shown in Table 5.

Rosiglitazone having the formula (XVI) was prepared according to the method described in *J. Med. Chem.* 1994, 37, 3997.

TABLE 5

| Compound | $EC_{50}$ (nM) |
|---|---|
| 3 | 250 |
| 4 | 230 |
| 5 | 95 |
| 6 | 50 |
| 7 | 25 |
| 8 | 75 |
| 10 | 150 |
| 11 | 100 |
| 15 | 230 |
| 18 | 45 |
| 19 | 20 |
| 24 | 50 |
| 25 | 12 |
| 26 | 40 |
| 32 | 250 |
| Rosiglitazone | 300 |

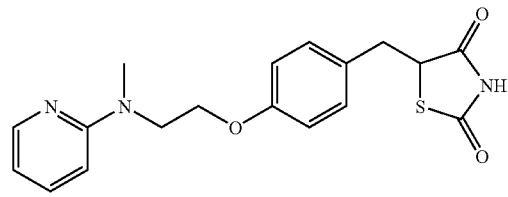

(XVI)

As shown in Table 5, the inventive compounds exhibited superior PPARγ activities over the comparative compound, rosiglitazone.

TEST EXAMPLE 2

Effectiveness in Lowering Blood Glucose Level

The effectiveness in lowering blood glucose level of the inventive compound was examined using ob/ob mice (male, 8-9 week old), a type 2 diabetes model animals which expresses signs of hyperglycemia and hyperinsulinemia, bred in house facilities of Korea Research Institute of Chemical Technology.

The hydrochloric acid salt of 1-hydroxy-6-(2-morpholine-4-yl-ethoxy)-1,3-diphenyl-1H-indene-2-carbo-xylic acid ethyl ester prepared in Example 8 was suspended in saline/0.2% Tween® 80. The resulting solution was intraperitoneally administered to the mice at a dose of 50 mg/kg, once a day for 5 days, or orally administered to the mice, at a dose of 100 mg/kg, twice a day for 14 days. Days 1, 3 and 5 were selected for intraperitoneal administration, and days 5, 10 and 14, for oral administration, to collect blood samples for measuring the blood glucose levels. The extent of inhibition of the inventive compound relative to the control (saline-0.2% Tween 80 in the absence of the compound) is shown in Table 6. Upon the completion of the oral administration for 14 days, the mice were fasted for 16 hrs to perform OGTT (Oral Glucose Tolerance Test) to determine the changes in insulin sensitivity induced by the oral administration. After administrating glucose to the mice at a dose of 2 g/kg orally, blood samples were collected at 0, 15, 30 60 and 120 minutes to measure blood glucose levels. The change in the total amount of blood glucose was computed over the 120 minute period to assess the extent of enhancing glucose clearance rates by the compound treatment. The results are shown in Table 6, as % inhibition of total amount of blood glucose by the compound treatment relative to the untreated group.

TABLE 6

| Classification | Extent of Inhibition (%) |
|---|---|
| Intraperitoneal Administration (50 mg/kg/day) | 32.0 |
| Oral Administration (100 mg/kg/day) | 23.7 |
| Oral Glucose Tolerance Test (Blood Glucose) | 10.2 |

Moreover, C57/BL6J mice (male, 4 week old) which received high fat diet (60% fat) for 10-11 weeks and showed hyperglycemia and insulin resistance were chosen to carry out similar experiments (oral administration for 14 days but once a day) as described above. The extents of suppression of blood glucose and insulin levels were measured as mentioned above. The results are shown in Table 7. To check possible adverse side effects caused by the administration of the compound, the weight, heart weight and liver weight of each mouse were measured. GPT and GOT values were also calculated by employing a kit available in the market. The results are listed in Table 8.

TABLE 7

| Classification | Inhibition Ratio (%) |
|---|---|
| Blood glucose level | 30.0 |
| Blood Insulin level | 44.6 |
| Oral Glucose Tolerance Test | 23.8(Glucose)/56.2(Insulin) |

TABLE 8

| | Weight (g) | Heart Weight (g) | Liver Weight (g) | GPT/GOT (karmen) |
|---|---|---|---|---|
| Standard (high-fat diet) | 40 ± 2.0 | 0.133 ± 0.012 | 1.42 ± 0.11 | 52 ± 10/ 48 ± 11 |
| The Inventive Compound | 37 ± 2.0 | 0.117 ± 0.012 | 1.22 ± 0.10 | 47 ± 6.5/ 35 ± 6.2 |
| Rosiglitazone | 40 ± 1.6 | 0.133 ± 0.004 | 1.35 ± 0.14 | 79 ± 8.3/ 40 ± 7.1 |

As shown in Tables 6, 7, and 8, the inventive compound has an excellent effect in lowering both blood glucose and insulin levels, when it is administered by either orally or intraperitoneally with no side effects such as weight gain, hepatotoxicity or cardiotoxicity.

While the invention has been described with respect to the above specific embodiments, it should be recognized that various modifications and changes may be made to the invention by those skilled in the art which also fall within the scope of the invention as defined by the appended claims.

What is claimed is:

1. An indene compound defined by formula (I) or a pharmaceutically acceptable salt thereof:

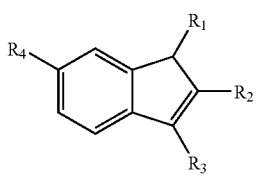

(I)

wherein, $R_1$ is —OCH$_3$, —OC$_2$H$_5$, —NH$_2$, —NHCOCH$_3$, —NHCOC$_2$H$_5$, —N(C$_2$H$_5$)$_2$, —NHC$_2$H$_5$,

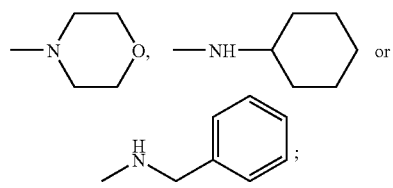

$R_2$ is CO$_2$R$^a$, CONHR$^b$ or CN;
$R_3$ is phenyl; and
$R_4$ is —OCH$_3$, —O(CH$_2$)$_3$R$^c$, —O(CH$_2$)$_2$R$^d$, —CH$_2$R$^d$ or

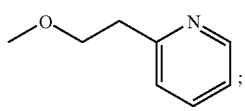

in which
$R^a$ is H, methyl or ethyl;
$R^b$ is cyclohexyl;
$R^c$ is phenyl; and
$R^d$ is

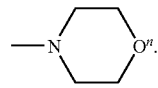

2. The compound of claim 1, which is selected from the group consisting of:

1,6-dimethoxy-3-phenyl-1H-indene-2-carboxylic acid ethyl ester,
1-ethoxy-6-methoxy-3-phenyl-1H-indene-2-carboxylic acid ethyl ester,
1-amino-6-methoxy-3-phenyl-1H-indene-2-carboxylic acid ethyl ester,
1-amino-3-phenyl-6-(3-phenyl-propoxy)-1H-indene-2-carboxylic acid ethyl ester,
1-amino-6-(2-morpholin-4-yl-ethoxy)-3-phenyl-1H-indene-2-carboxylic acid cyclohexyl amide,
1-amino-3-phenyl-6-(3-phenyl-propoxy)-1H-indene-2-carbonitrile,
1-acetylamino-6-methoxy-3-phenyl-1H-indene-2-carboxylic acid ethyl ester,
6-methoxy-3-phenyl-1-propionylamino-1H-indene-2-carboxylic acid ethyl ester,
1-acetylamino-3-phenyl-6-(3-phenyl-propoxy)-1H-indene-2-carboxylic acid ethyl ester,
1-acetylamino-6-(2-morpholin-4-yl-ethoxy)-3-phenyl-1H-indene-2-carboxylic acid cyclohexyl amide,
1-diethylamino-6-methoxy-3-phenyl-1H-indene-2-carboxylic acid ethyl ester,
1-ethylamino-6-methoxy-3-phenyl-1H-indene-2-carboxylic acid ethyl ester,
6-methoxy-1-morpholin-4-yl-3-phenyl-1H-indene-2-carboxylic acid ethyl ester,
1-benzyl amino-6-methoxy-3-phenyl-1H-indene-2-carboxylic acid ethyl ester, and
1-cyclohexyl amino-6-methoxy-3-phenyl-1H-indene-2-carboxylic acid ethyl ester.

3. A pharmaceutical composition comprising a compound according to claim 1 and a pharmaceutically acceptable carrier.

* * * * *